(12) United States Patent
Lahaye et al.

(10) Patent No.: US 8,198,510 B2
(45) Date of Patent: Jun. 12, 2012

(54) BS3 RESISTANCE GENE AND METHODS OF USE

(75) Inventors: Thomas Lahaye, Halle (DE); Ulla Bonas, Halle (DE); Patrick Römer, Riesdorf (DE)

(73) Assignee: Two Blades Foundation, Evanston, IL (US)

( * ) Notice: Subject to any disclaimer, the term of this patent is extended or adjusted under 35 U.S.C. 154(b) by 689 days.

(21) Appl. No.: 12/238,682

(22) Filed: Sep. 26, 2008

(65) Prior Publication Data
US 2009/0133158 A1 May 21, 2009

Related U.S. Application Data

(60) Provisional application No. 60/976,017, filed on Sep. 28, 2007.

(51) Int. Cl.
*A01H 5/00* (2006.01)
*A01H 5/10* (2006.01)
*C12N 15/09* (2006.01)
*C12N 15/82* (2006.01)
*C12N 15/29* (2006.01)

(52) U.S. Cl. ........ 800/279; 800/278; 800/298; 800/295; 800/320.1; 800/320.2; 800/320.3; 800/317; 800/312; 800/313; 800/306; 800/317.1; 800/317.3; 800/317.4; 800/314; 800/316; 435/320.1; 435/468; 536/23.2; 536/24.1

(58) Field of Classification Search ........................ None
See application file for complete search history.

(56) References Cited

OTHER PUBLICATIONS

Jordan, T., et al., "Physical delimitation of the pepper *Bs3* resistance gene specifying recognition of the AvrBs3 protein from *Xanthomonas campestris* pv. *vesicatoria*," *Theor Appl Genet*, 2006, vol. 113, pp. 895-905.
Kousik, C.S., et al., "Development of Bacterial Spot on Near-Isogenic Lines of Bell Pepper Carrying Gene Pyramids Composed of Defeated Major Resistance Genes," *Phytopathology*, 1999, vol. 89(11), pp. 1066-1072.
Pierre, M., et al., "High-resolution genetic mapping of the pepper resistance locus *Bs3* governing recognition of the *Xanthomonas campestris* pv *vesicatora* AvrBs3 protein," *Theor Appl Genet*, 2000, vol. 101, pp. 255-263.
Römer, P., et al., "Plant Pathogen Recognition Mediated by Promoter Activation of the Pepper *Bs3* Resistance Gene," *Science*, (2007), vol. 318, pp. 645-648.

*Primary Examiner* — Medina A Ibrahim
(74) *Attorney, Agent, or Firm* — Alston & Bird LLP

(57) ABSTRACT

Isolated nucleic acid molecules that confer resistance to the plant pathogen *Xanthomonas campestris* are provided. These molecules may be introduced into plants that are otherwise susceptible to infection by this bacterium in order to enhance the resistance of the plant to this plant pathogen. Additionally provided are isolated polypeptides and isolated nucleic acid molecules comprising plant promoters. Methods of using the nucleic acid molecules to increase the resistance of plants to pathogens and to express genes of interest in plants are provided.

38 Claims, 14 Drawing Sheets

Figure 2:
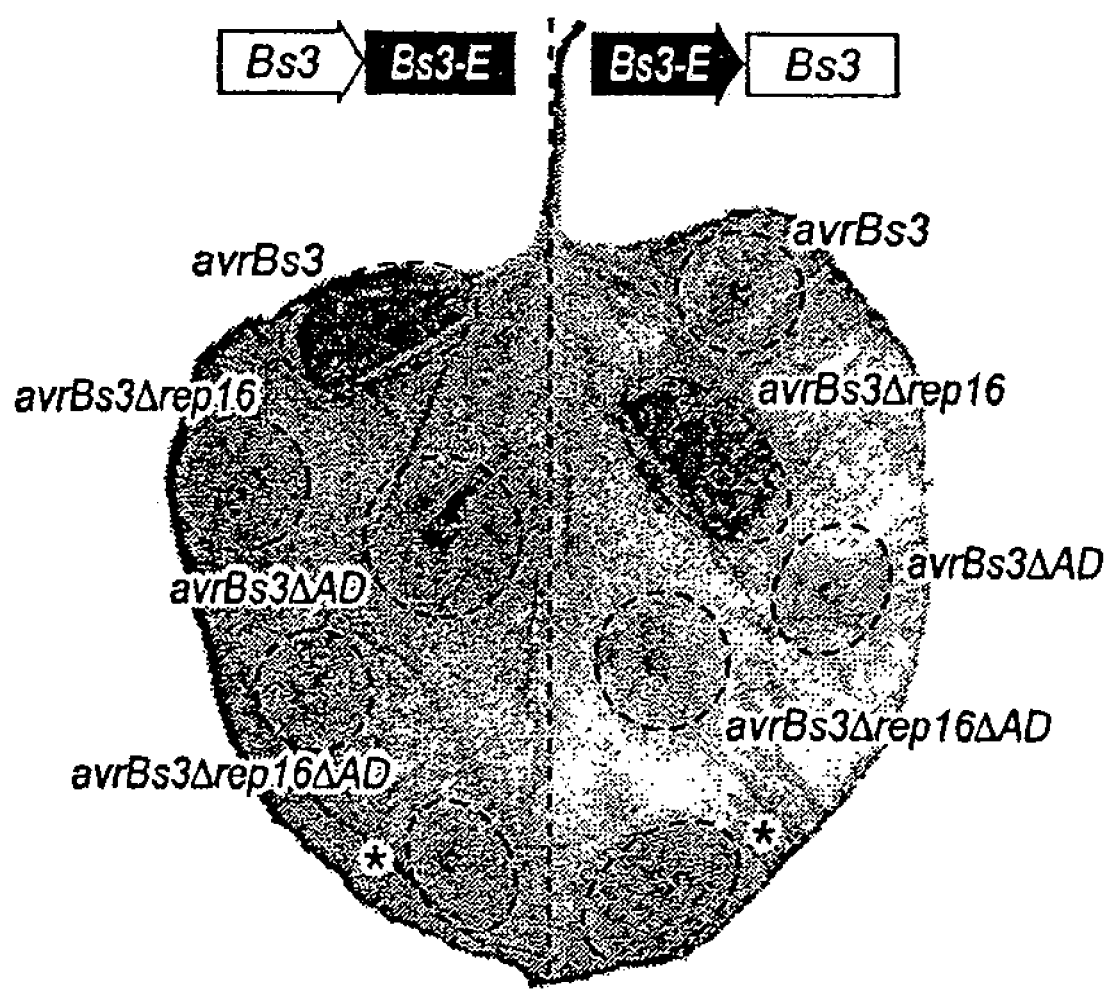

Figure 1
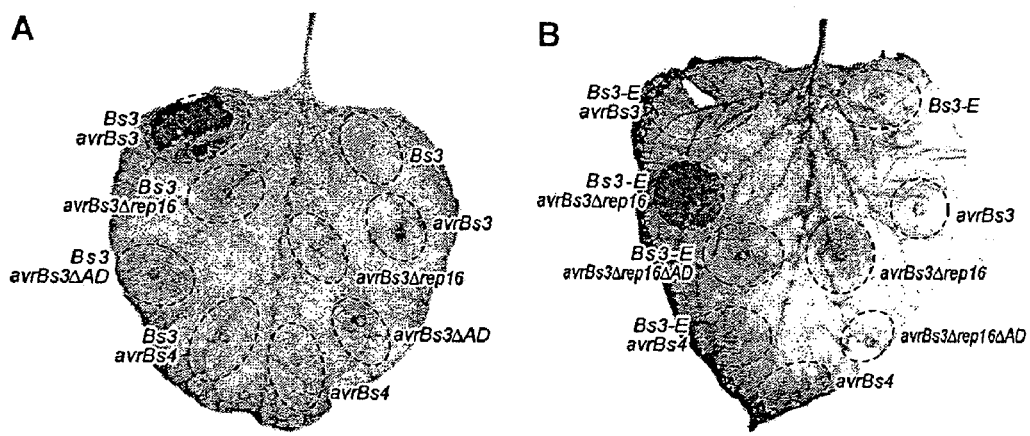
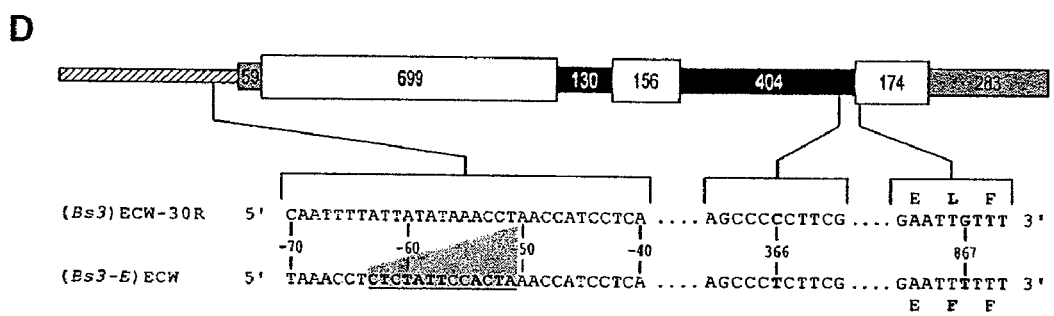

Figure 5

```
               GTTCTTGTCACCCGCTAAATCTATCAAAACACAAGTAGTCCTAGTTGCACATATATTTC

M   M   N   Q   N   C   F   N   S   C   S   P   L   T   V   D   A   L   E   P    20
   ATGATGAATCAGAATTGCTTTAATTCTTGTTCACCTCTAACTGTTGATGCACTTGAACCA   60

K   K   S   S   C   A   A   K   C   I   Q   V   N   G   P   L   I   V   G   A    40
   AAAAAATCCTCTTGTGCTGCTAAATGCATACAAGTAAATGGTCCTCTTATTGTTGGAGCT  120

G   P   S   G   L   A   T   A   A   V   L   K   Q   Y   S   V   P   Y   V   I    60
   GGCCCTTCAGGCCTGGCTACTGCTGCCGTCCTTAAGCAATACAGTGTTCCGTATGTAATC  180

I   E   R   A   D   C   I   A   S   L   W   Q   H   K   T   Y   D   R   L   R    80
   ATTGAACGCGCGGACTGCATTGCTTCTCTGTGGCAACACAAGACCTACGATCGGCTTAGG  240

L   N   V   P   R   Q   Y   C   E   L   P   G   L   P   F   P   P   D   F   P   100
   CTTAACGTGCCACGACAATACTGCGAATTGCCTGGCTTGCCATTTCCACCAGACTTTCCA  300

E   Y   P   T   K   N   Q   F   I   S   Y   L   V   S   Y   A   K   H   F   E   120
   GAGTATCCAACCAAAAACCAATTCATCAGCTACCTCGTATCTTATGCAAAGCATTTCGAG  360

I   K   P   Q   L   N   E   S   V   N   L   A   G   Y   D   E   T   C   G   L   140
   ATCAAACCACAACTCAACGAGTCAGTAAACTTAGCTGGATATGATGAGACATGTGGTTTA  420

W   K   V   K   T   V   S   E   I   N   G   S   T   S   E   Y   M   C   K   W   160
   TGGAAGGTGAAAACAGTTTCTGAAATCAATGGTTCAACCTCTGAATACATGTGTAAGTGG  480

L   I   V   A   T   G   E   N   A   E   M   I   V   P   E   F   E   G   L   Q   180
   CTTATTGTGGCCACAGGAGAGAATGCTGAGATGATAGTGCCCGAATTCGAAGGATTGCAA  540

II
    D   F   G   G   Q   V   I   H   A   C   E   Y   K   T   G   E   Y   Y   T   G   200
   GATTTTGGTGGCCAGGTTATTCATGCTTGTGAGTACAAGACTGGGGAATACTATACTGGA  600

III
    E   N   V   L   A   V   G   C   G   N   S   G   I   D   I   S   L   D   L   S   220
   GAAAATGTGCTGGCGGTTGGCTGTGGCAATTCCGGGATCGATATCTCACTTGATCTTTCC  660

Q   H   N   A   N   P   F   M   V   V   R   S   S   V   Q   G   R   N   F   P   240
   CAACATAATGCAAATCCATTCATGGTAGTTCGAAGCTCGGTACAGGGTCGTAATTTCCCT  720
                                                  ▲
    E   E   I   N   I   V   P   A   I   K   K   F   T   Q   G   K   V   E   F   V   260
   GAGGAAATAAACATAGTTCCAGCAATCAAGAAATTTACTCAAGGAAAAGTAGAATTTGTT  780

IV
    N   G   Q   I   L   E   I   D   S   V   I   L   A   T   G   Y   T   S   N   V   280
   AATGGACAAATTCTAGAGATCGACTCTGTTATCTTGGCAACTGGTTATACCAGCAATGTA  840

T   S   W   L   M   E   S   L   F   S   R   E   G   C   P   K   S   P   F   300
   ACTTCTTGGTTAATGGAGAGTGAATTGTTTTCAAGGGAGGGATGTCCAAAAAGCCCATTC  900
                             ▲       T
    P   N   G   W   K   G   E   D   G   L   Y   A   V   G   F   T   G   I   G   L   320
   CCAAATGGTTGGAAGGGGGAGGATGGTCTCTATGCAGTTGGATTTACAGGAATAGGACTG  960

F   G   A   S   I   D   A   T   N   V   A   Q   D   I   A   K   I   W   K   E   340
   TTTGGTGCTTCTATAGATGCCACTAATGTTGCACAAGATATTGCCAAAATTTGGAAAGAA 1020

Q   M   *                                                                       342
   CAAATGTAGCACAAGAATCATAATCAATCTGTTGGATGCATGCCATGGAGAAGAAGCAAG 1080

TTACTTTTCTCATGTCAAGAAAATAAGATTTTTTTTTTCTT
```

Figure 6

```
                                      *  *  *
Bs3                    1 MMNQNCFNSCSPLTVDALEPKKSSCAAKCHQVNGPLIIGAGPSGLATAAVKQ--YSPPY
At YUCCA01 (AT4G32540) 1 ---------------MESHPHNKTDQTQHIDLVEGPIIIGAGPSGLAISACSS--RGPS
At FMO1 (At1G19250)    1 -----------------MASNYDKITSSHAIIGAGVSGLAAIKVH----HNP
Hs FMO1 (NP 002012)    1 ---------------------AKKVALKGAGVSGLAAIKCCLE--EGEP
Sc FMO1 (NP 012046)    1 -----------------MTVNDKIRAIAIIGGPGGLAAAKVFSQSLPNFEI

Bs3                   59 VIIERADCESLVQH---------KHYDERKNPPQYCELPGLPFFPDEF--EYPTNG
At YUCCA01 (AT4G32540) 45 LALERSDSIISLWKS---------KHYDERENIPPKHFCRLPLLDFPYEG--KYPSNE
At FMO1 (At1G19250)   35 TYFFASDSVGGWWS---------CHYTTAHESAHVDYESSGDFPHNNRDDTTSGPYLE
Hs FMO1 (NP002012)    28 TCFERSDDHGGLWHFTEHVEEGRASLVKSHVSNSCHEMSCHSDFPFPEDEH--NHVPNSQ
Sc FMO1 (NP012046)    35 EIIVEDYDIGGHYPEQKSDGR-VMYDILETNKSHKLMQESGFPPHDNVH--LYHSRR

Bs3                  108 HISYLVSYAKHFFEKPQFMES-----VNLACYDEH--------------CHLHKVKHVS
At YUCCA01 (AT4G32540) 94 HLAYLESYASHHHAPRFHKN-----VQNAHYDSS--------------SGFHRVKHH-
At FMO1 (At1G19250)   86 IHSYLESYAKHFHLHFKFGSKVIEVRFIHDGEHPQMVDLGAYGNLLPGKPVHEVAVQI
Hs FMO1 (NP002012)    86 HIHYLKMYAHHFHDLLHHLHFKTKVCSVTKCSDSAV-----------SGQHVHHH
Sc FMO1 (NP012046)    92 IWHYLKAYYKTHIANKDAISIHFS--TEVTYLKKK-----------NSCMHHTSKD

*** *  *  *
Bs3                  148 HINGSTHLHMCKHLVHTCGHNMBI-HPHBHGL--QDH-GGQHHACHHTCH------Y
At YUCCA01 (AT4G32540) 133 ----HNHHILSKHVNALPY-FPHIFQR--KKHSGCKIHASEHVSGH------E
At FMO1 (At1G19250)  146 GDSGHIQWHAFEHVHMCHGKYHDFHRHAHIKKGPEMFQCKHAHHCMHYCKLHKEEASTL
Hs FMO1 (NP002012)   131 HEKQHHSAIHDAVMVCTHFLTHPYH-HDSHPGI--NAH-KCQYFHGRQHHHPH------I
Sc FMO1 (NP012046)   135 HLRTTKSHDFVIHASHCHYSVPKH-TNIAGLD--LWDNKGAFHSKHHNCH------F

*  *  *
Bs3                  198 HTGEMVHAWGCGNSGHDISHLHQHN-----ANPHHVVR----------------
At YUCCA01 (AT4G32540) 180 HHRQHVLVVGCNSGHHLSHLHVRHH-----ASPHHWRNTVHVHPHEIHG--VSTFGVG
At FMO1 (At1G19250)  206 LSGCHVAHHGFKKSHHHAHLSALAHQGEGGKACTHHWRTTHWGHPHYWHGLPFFLFYS
Hs FMO1 (NP002012)   181 HYDHVLVHGMGNSGHHHAHHLA-----EKVIHSTTGGWVHSH--HF-DSGYPWD
Sc FMO1 (NP012046)   186 AHHHVVVGNHSSGQDIANOHHTVA-----KKVHNSHHEP----------

Bs3                  232 ------SSHOGHN----------
At YUCCA01 (AT4G32540) 233 MTLLKCLPLRLVDKFLLLHANLSFGNTDRLGLRRPKTGPHELKNHTGHSPVLDVGAMSLI
At FMO1 (At1G19250)  266 SRASQFLHDRPNQSFLRTHFCLLFSLLRAVVSKFIESYVHWKLPHEKYGLKPNHSFEEDY
Hs FMO1 (NP002012)   232 MVFMTRFQNMLRNSLPTPHVTWLMERKINNWLNHANYGLHPEDRTQLHEFVLNDELPGRI
Sc FMO1 (NP012046)   222 ---------------------ASNHLHA-----------

****  *  ****
Bs3                  239 FPEEHNIHHA--HHKFTQGKVHHV-NHQILH-HDSHHHLATGYTSNVTSHHMEHELFSRHG
At YUCCA01 (AT4G32540) 293 RHGMHQHHEG--HHHITKKGAKHM-DCQERH-FHSHHFAHGYKSNVHHTAHQGGDFFTDHG
At FMO1 (At1G19250)  326 ASCCGHAHHENFFEHADKGMHRHKKSSKWNFYEHGHHHEDCIHLEADVVHLAHGYDGKKK
Hs FMO1 (NP002012)   292 IHGKHHHRHS--HHLVKENSHIHN-NTSKEHPTDILHHATGYHFAFH-HDESHVVKVEHG
Sc FMO1 (NP012046)   229 KLIETVQTID--SAHWKNRSHTLS-DHRVLQNHHYHHHFAHGYYYSFH-HEPSVRLEVLH

Bs3                  295 CP---KSFHHNGWHG--------EDHLYAHGHTGIHHFHA--------SHHA
At YUCCA01 (AT4G32540) 349 MP---HTPHHNGWHG--------GKHLYTHGHTRRHLLHT--------ASHA
At FMO1 (At1G19250)  386 LKAIVPPHHRTWHEFPSG---------VMPHYRHTIHPLIPNMHFVHY-------HOSSS
Hs FMO1 (NP002012)   348 QASLYHYIHHAHHQKPTLAIIGLIKPLGSMHPTHETQARHAVRVHHKGVNKLPPSHHHHE
Sc FMO1 (NP012046)   285 EGVTGDKHSSVNLHHNLWEHMIYVKDPTLSFHLTPQLVHHPLSEHQHA-------HMHHV

Bs3                  328 TNVAQHHAKIHK-----EQH----------
At YUCCA01 (AT4G32540) 382 VKIAGHHGDQHR------DEHKGSTRNMCSSRFVHTSKS----------
At FMO1 (At1G19250)  430 NLHTSHHHRSMHLS----RLHDEKFRLPSKHKMLDQFLKEMEVHRNSSRFYKRHCHSTFSI
Hs FMO1 (NP002012)   408 INARKHNKPSHFGLCYCKAHQSDYITYIDHLLTHINAKPNLFHMLLTDPHLALTHFFGPC
Sc FMO1 (NP012046)   338 FCKSLPHTTTHDS----NACGTHNFPKGKHLEYHAELQELLNHIPRRVGHFEPVHWDDRL

Bs3                      ----
At YUCCA01 (AT4G32540)   ----
At FMO1 (At1G19250)  486 QHADDMCNDMGLNPWRHSNFHLEAFSPYGSQDYRLGQEEKEDMTA----------
Hs FMO1 (NP002012)   468 SPYQFRLTGPGKWEGAHNAIHTQWDRTFKVIKARVVQESPSPFESFLKVFSFLALLVAIF
Sc FMO1 (NP012046)   394 IDLRN---SSYTDKEDHNVLHAEHAQALKKKKAPYFLPAPHT----------

Bs3                      ----
At YUCCA01 (AT4G32540)   ----
At FMO1 (At1G19250)      ----
Hs FMO1 (NP002012)   528 LIFL
Sc FMO1 (NP012046)       ----
```

Figure 8

Figure 12
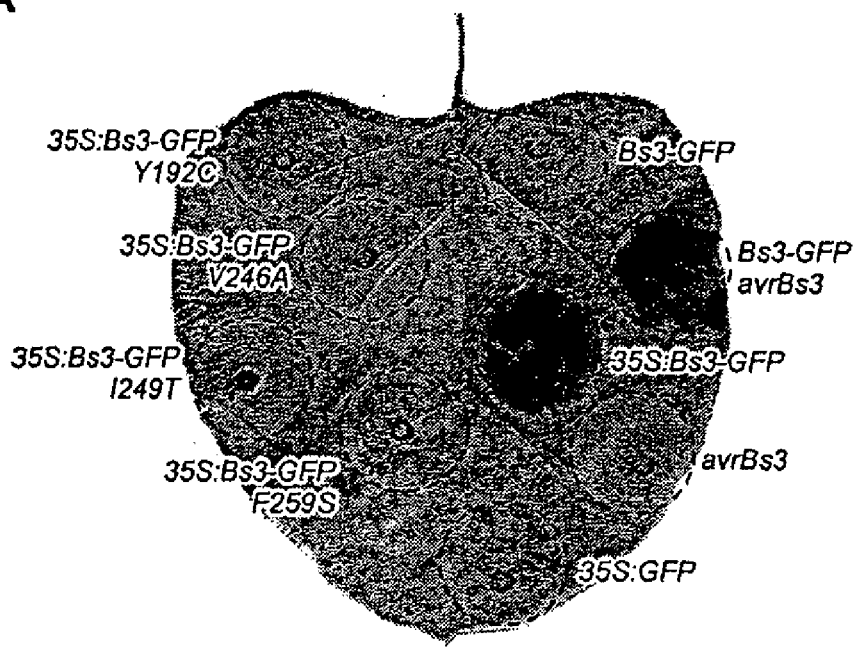
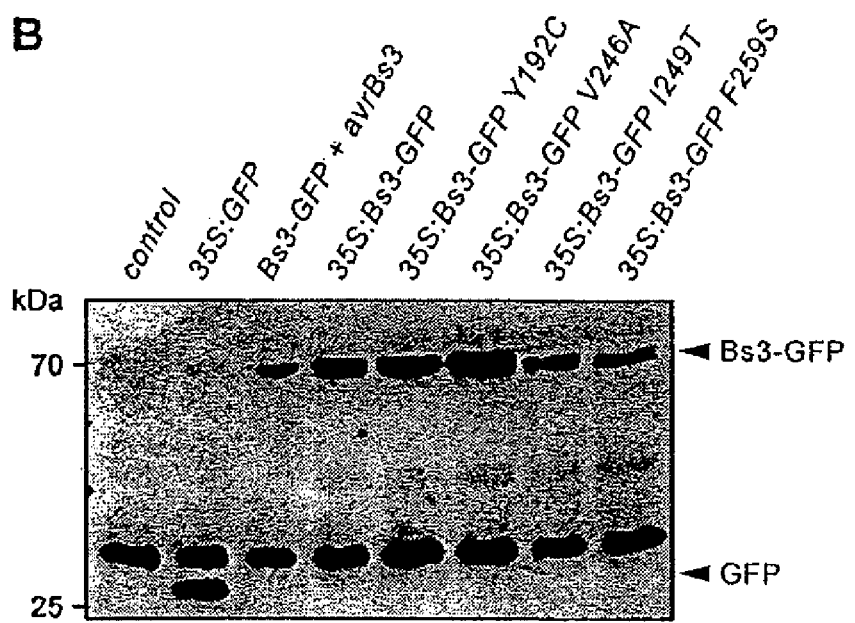

SEQUENCE LISTING

```
<160> NUMBER OF SEQ ID NOS: 25

<210> SEQ ID NO 1
<211> LENGTH: 1029
<212> TYPE: DNA
<213> ORGANISM: Capsicum annuum
<220> FEATURE:
<221> NAME/KEY: CDS
<222> LOCATION: (1)...(1026)
```

```
<400> SEQUENCE: 1 atg atg aat cag aat tgc ttt aat tct tgt tca cct cta act gtt gat        48
Met Met Asn Gln Asn Cys Phe Asn Ser Cys Ser Pro Leu Thr Val Asp
1               5                   10                  15 gca ctt gaa cca aaa aaa tcc tct tgt gct gct aaa tgc ata caa gta        96
Ala Leu Glu Pro Lys Lys Ser Ser Cys Ala Ala Lys Cys Ile Gln Val
            20                  25                  30 aat ggt cct ctt att gtt gga gct ggc cct tca ggc ctg gct act gct      144
Asn Gly Pro Leu Ile Val Gly Ala Gly Pro Ser Gly Leu Ala Thr Ala
        35                  40                  45 gcc gtc ctt aag caa tac agt gtt ccg tat gta atc att gaa cgc gcg      192
Ala Val Leu Lys Gln Tyr Ser Val Pro Tyr Val Ile Ile Glu Arg Ala
50                  55                  60 gac tgc att gct tct ctg tgg caa cac aag acc tac gat cgg ctt agg      240
Asp Cys Ile Ala Ser Leu Trp Gln His Lys Thr Tyr Asp Arg Leu Arg
65                  70                  75                  80 ctt aac gtg cca cga caa tac tgc gaa ttg cct ggc ttg cca ttt cca      288
Leu Asn Val Pro Arg Gln Tyr Cys Glu Leu Pro Gly Leu Pro Phe Pro
                85                  90                  95 cca gac ttt cca gag tat cca acc aaa aac caa ttc atc agc tac ctc      336
Pro Asp Phe Pro Glu Tyr Pro Thr Lys Asn Gln Phe Ile Ser Tyr Leu
            100                 105                 110 gta tct tat gca aag cat ttc gag atc aaa cca caa ctc aac gag tca      384
Val Ser Tyr Ala Lys His Phe Glu Ile Lys Pro Gln Leu Asn Glu Ser
        115                 120                 125 gta aac tta gct gga tat gat gag aca tgt ggt tta tgg aag gtg aaa      432
Val Asn Leu Ala Gly Tyr Asp Glu Thr Cys Gly Leu Trp Lys Val Lys
    130                 135                 140 aca gtt tct gaa atc aat ggt tca acc tct gaa tac atg tgt aag tgg      480
Thr Val Ser Glu Ile Asn Gly Ser Thr Ser Glu Tyr Met Cys Lys Trp
145                 150                 155                 160 ctt att gtg gcc aca gga gag aat gct gag atg ata gtg ccc gaa ttc      528
Leu Ile Val Ala Thr Gly Glu Asn Ala Glu Met Ile Val Pro Glu Phe
                165                 170                 175 gaa gga ttg caa gat ttt ggt ggc cag gtt att cat gct tgt gag tac      576
Glu Gly Leu Gln Asp Phe Gly Gly Gln Val Ile His Ala Cys Glu Tyr
            180                 185                 190 aag act ggg gaa tac tat act gga gaa aat gtg ctg gcg gtt ggc tgt      624
Lys Thr Gly Glu Tyr Tyr Thr Gly Glu Asn Val Leu Ala Val Gly Cys
        195                 200                 205 ggc aat tcc ggg atc gat atc tca ctt gat ctt tcc caa cat aat gca      672
Gly Asn Ser Gly Ile Asp Ile Ser Leu Asp Leu Ser Gln His Asn Ala
    210                 215                 220 aat cca ttc atg gta gtt cga agc tcg gta cag ggt cgt aat ttc cct      720
Asn Pro Phe Met Val Val Arg Ser Ser Val Gln Gly Arg Asn Phe Pro
225                 230                 235                 240 gag gaa ata aac ata gtt cca gca atc aag aaa ttt act caa gga aaa      768
Glu Glu Ile Asn Ile Val Pro Ala Ile Lys Lys Phe Thr Gln Gly Lys
                245                 250                 255 gta gaa ttt gtt aat gga caa att cta gag atc gac tct gtt atc ttg      816
Val Glu Phe Val Asn Gly Gln Ile Leu Glu Ile Asp Ser Val Ile Leu
            260                 265                 270 gca act ggt tat acc agc aat gta act tct tgg tta atg gag agt gaa      864
Ala Thr Gly Tyr Thr Ser Asn Val Thr Ser Trp Leu Met Glu Ser Glu
        275                 280                 285 ttg ttt tca agg gag gga tgt cca aaa agc cca ttc cca aat ggt tgg      912
Leu Phe Ser Arg Glu Gly Cys Pro Lys Ser Pro Phe Pro Asn Gly Trp
    290                 295                 300
```

```
aag ggg gag gat ggt ctc tat gca gtt gga ttt aca gga ata gga ctg      960
Lys Gly Glu Asp Gly Leu Tyr Ala Val Gly Phe Thr Gly Ile Gly Leu
305                 310                 315                 320 ttt ggt gct tct ata gat gcc act aat gtt gca caa gat att gcc aaa     1008
Phe Gly Ala Ser Ile Asp Ala Thr Asn Val Ala Gln Asp Ile Ala Lys
                325                 330                 335 att tgg aaa gaa caa atg tag                                         1029
Ile Trp Lys Glu Gln Met
            340
```

<210> SEQ ID NO 2
<211> LENGTH: 342
<212> TYPE: PRT
<213> ORGANISM: Capsicum annuum

<400> SEQUENCE: 2

```
Met Met Asn Gln Asn Cys Phe Asn Ser Cys Ser Pro Leu Thr Val Asp
1               5                   10                  15

Ala Leu Glu Pro Lys Lys Ser Ser Cys Ala Ala Lys Cys Ile Gln Val
            20                  25                  30

Asn Gly Pro Leu Ile Val Gly Ala Gly Pro Ser Gly Leu Ala Thr Ala
        35                  40                  45

Ala Val Leu Lys Gln Tyr Ser Val Pro Tyr Val Ile Glu Arg Ala
    50                  55                  60

Asp Cys Ile Ala Ser Leu Trp Gln His Lys Thr Tyr Asp Arg Leu Arg
65                  70                  75                  80

Leu Asn Val Pro Arg Gln Tyr Cys Glu Leu Pro Gly Leu Pro Phe Pro
                85                  90                  95

Pro Asp Phe Pro Glu Tyr Pro Thr Lys Asn Gln Phe Ile Ser Tyr Leu
            100                 105                 110

Val Ser Tyr Ala Lys His Phe Glu Ile Lys Pro Gln Leu Asn Glu Ser
        115                 120                 125

Val Asn Leu Ala Gly Tyr Asp Glu Thr Cys Gly Leu Trp Lys Val Lys
    130                 135                 140

Thr Val Ser Glu Ile Asn Gly Ser Thr Ser Glu Tyr Met Cys Lys Trp
145                 150                 155                 160

Leu Ile Val Ala Thr Gly Glu Asn Ala Glu Met Ile Val Pro Glu Phe
                165                 170                 175

Glu Gly Leu Gln Asp Phe Gly Gly Gln Val Ile His Ala Cys Glu Tyr
            180                 185                 190

Lys Thr Gly Glu Tyr Tyr Thr Gly Glu Asn Val Leu Ala Val Gly Cys
        195                 200                 205

Gly Asn Ser Gly Ile Asp Ile Ser Leu Asp Leu Ser Gln His Asn Ala
    210                 215                 220

Asn Pro Phe Met Val Val Arg Ser Ser Val Gln Gly Arg Asn Phe Pro
225                 230                 235                 240

Glu Glu Ile Asn Ile Val Pro Ala Ile Lys Lys Phe Thr Gln Gly Lys
                245                 250                 255

Val Glu Phe Val Asn Gly Gln Ile Leu Glu Ile Asp Ser Val Ile Leu
            260                 265                 270

Ala Thr Gly Tyr Thr Ser Asn Val Thr Ser Trp Leu Met Glu Ser Glu
        275                 280                 285

Leu Phe Ser Arg Glu Gly Cys Pro Lys Ser Pro Phe Pro Asn Gly Trp
    290                 295                 300

Lys Gly Glu Asp Gly Leu Tyr Ala Val Gly Phe Thr Gly Ile Gly Leu
305                 310                 315                 320
```

```
Phe Gly Ala Ser Ile Asp Ala Thr Asn Val Ala Gln Asp Ile Ala Lys
              325                 330                 335

Ile Trp Lys Glu Gln Met
            340

<210> SEQ ID NO 3
<211> LENGTH: 1026
<212> TYPE: DNA
<213> ORGANISM: Capsicum annuum

<400> SEQUENCE: 3
atgatgaatc agaattgctt taattcttgt tcacctctaa ctgttgatgc acttgaacca      60
aaaaaatcct cttgtgctgc taaatgcata caagtaaatg gtcctcttat tgttggagct     120
ggcccttcag gcctggctac tgctgccgtc cttaagcaat acagtgttcc gtatgtaatc     180
attgaacgcg cggactgcat tgcttctctg tggcaacaca agacctacga tcggcttagg     240
cttaacgtgc cacgacaata ctgcgaattg cctggcttgc catttccacc agactttcca     300
gagtatccaa ccaaaaacca attcatcagc tacctcgtat cttatgcaaa gcatttcgag     360
atcaaaccac aactcaacga gtcagtaaac ttagctggat atgatgagac atgtggttta     420
tggaaggtga aaacagtttc tgaaatcaat ggttcaacct ctgaatacat gtgtaagtgg     480
cttattgtgg ccacaggaga gaatgctgag atgatagtgc cgaattcga aggattgcaa     540 gattttggtg ccaggttat tcatgcttgt gagtacaaga ctggggaata ctatactgga     600
gaaaatgtgc tggcggttgg ctgtggcaat tccgggatcg atatctcact tgatctttcc     660
caacataatg caaatccatt catggtagtt cgaagctcgg tacagggtcg taatttccct     720
gaggaaataa acatagttcc agcaatcaag aaatttactc aaggaaaagt agaatttgtt     780
aatggacaaa ttctagagat cgactctgtt atcttggcaa ctggttatac cagcaatgta     840
acttcttggt taatggagag tgaattgttt tcaaggagg gatgtccaaa aagcccattc     900
ccaaatggtt ggaaggggga ggatggtctc tatgcagttg gatttacagg aataggactg     960
tttggtgctt ctatagatgc cactaatgtt gcacaagata ttgccaaaat ttggaaagaa    1020
caaatg                                                               1026

<210> SEQ ID NO 4
<211> LENGTH: 3331
<212> TYPE: DNA
<213> ORGANISM: Capsicum annuum
<220> FEATURE:
<221> NAME/KEY: promoter
<222> LOCATION: (1)...(1087)
<220> FEATURE:
<221> NAME/KEY: exon
<222> LOCATION: (1088)...(1786)
<220> FEATURE:
<221> NAME/KEY: intron
<222> LOCATION: (1787)...(1916)
<220> FEATURE:
<221> NAME/KEY: exon
<222> LOCATION: (1917)...(2072)
<220> FEATURE:
<221> NAME/KEY: intron
<222> LOCATION: (2073)...(2476)
<220> FEATURE:
<221> NAME/KEY: exon
<222> LOCATION: (2477)...(2650)
<220> FEATURE:
<221> NAME/KEY: 5'UTR
<222> LOCATION: (2651)...(3331)
<220> FEATURE:
<221> NAME/KEY: misc_feature
<222> LOCATION: (968)...(982)
<223> OTHER INFORMATION: UPA Box
```

```
<400> SEQUENCE: 4
atttcttcta tgtgccttgt gtccaaaaga tgtttcagaa gttcgcgttg ggaagttgtc      60
accctacgga atagcagcat taaggcacat cagagatttt ttgggtgtta agtttgtcat     120
gaaacctgat gcctccacag gaactgtcaa tctcatgtgt cttggctctg gttttcagaa     180
tttatccaga aaagtatcat gataaattaa tggtgtctgt gtttggtggc ttagagtgac     240
ggctagatca acatctttgg gatgccttgt ggagtgaaat caagcatact ttatcatagg     300
cgaaattttt tgttgtggtt tgctgcttgt aatgagagag tgatatagga agcaaatgtg     360
gagatcacat ttgctcatct ccttgttgcg ttgaaacttt tggtgtcaag agttctaatt     420
cacatgtatt tgaagattcc tcatatgctg cttttgtttc taattatttt ttctagtaag     480
aaaacatttg ttcctgagtt tccaactaga aaaaaatatc aagtaaaata gaattcaatc     540
atttccctta ccaacgcttg gtactgccaa ccgcaacaaa gaattaatgc aaaacaacag     600
tctattaata tcaacctaga ctaaactcct tagtttttact ttgaaatgcg aatgatacat     660
gacacattag attgtacttg cttttttacca cagatacaac gatacatttg tatatctttt     720
cccttatagc aaactctaat atatcatagt caagctaacg aaacttatgc aagggaaata     780
tgaaattagt atgcaagtaa actcaaagaa ctaatcattg aactgaaaga tcaatatatc     840
aaaaaaaaaa aaaaaacaat aaaaccgttt aaccgataga ttaaccatttt ctggttcagt     900
ttatgggtta accacaatt tgcacaccct ggttaaacaa tgaacacgtt tgcctgacca      960
atttttattat ataaacctaa ccatcctcac aacttcaagt tatcatcccc tttctctttt    1020
ctcctcttgt tcttgtcacc cgctaaatct atcaaaacac aagtagtcct agttgcacat    1080
atatttcatg atgaatcaga attgctttaa ttccttgttca cctctaactg ttgatgcact    1140
tgaaccaaaa aaatcctctt gtgctgctaa atgcatacaa gtaaatggtc ctcttattgt    1200
tggagctggc ccttcaggcc tggctactgc tgccgtcctt aagcaataca gtgttccgta    1260
tgtaatcatt gaacgcgcgg actgcattgc ttctctgtgg caacacaaga cctacgatcg    1320
gcttaggctt aacgtgccac gacaatactg cgaattgcct ggcttgccat ttccaccaga    1380
cttttccagag tatccaacca aaaaccaatt catcagctac ctcgtatctt atgcaaagca    1440
tttcgagatc aaaccacaac tcaacgagtc agtaaactta gctggatatg atgagacatg    1500
tggtttatgg aaggtgaaaa cagtttctga atcaatggt tcaacctctg aatacatgtg      1560
taagtggctt attgtggcca caggagagaa tgctgagatg atagtgcccg aattcgaagg    1620
attgcaagat tttggtggcc aggttattca tgcttgtgag tacaagactg gggaatacta    1680
tactggagaa aatgtgctgg cggttggctg tggcaattcc gggatcgata tctcacttga    1740
tctttcccaa cataatgcaa atccattcat ggtagttcga agctcggtaa gttttatatt    1800
caataagtat tattttttcaa gtaacactag aaagtgatct tgtatctttc atttgctcgc    1860
atgaatatat tatattcaca catgaatgat atcatctagt tttgttaatc tttcaggtac    1920
agggtcgtaa tttccctgag gaaataaaca tagttccagc aatcaagaaa tttactcaag    1980
gaaaagtaga atttgttaat ggacaaattc tagagatcga ctctgttatc ttggcaactg    2040
gttataccag caatgtaact tcttggttaa tggtaaggaa atacacaagt tttattttcta    2100
tgcctaatta aattggtgtt taatcataaa ttatatatag tactaagtat gataaaagct    2160
ccttcaacta taaaggatga tttagtcaaa tgaactctta atgaatgtag taattattta    2220
tggattcttg ttcacattcat gtaagttggt atctcattat cctgtggatt cttctttg     2280
agttattaat tagttagaat tcactataac cgtctttttt cttttaccct ttcctcatac    2340
```

-continued

```
cttttttgttc ttttgataac tcgaactcac aatcttaaga ttgggaataa ggggctcttt      2400
accatctgag caactttctc tcgttctata atagcccct tcgaaatttg gtctaatgag        2460
aattttactg atacaggaga gtgaattgtt ttcaagggag ggatgtccaa aaagcccatt       2520
cccaaatggt tggaagggg aggatggtct ctatgcagtt ggatttacag gaataggact        2580
gtttggtgct tctatagatg ccactaatgt tgcacaagat attgccaaaa tttggaaaga      2640
acaaatgtag cacaagaatc ataatcaatc tgttggatgc atgccatgga gaagaagcaa     2700 gttactttc tcatgtcaag aaaataagat tttttttttt cttcctgtaa tattactggg       2760
attggatatt ctcccagttg cctttgttt gatttgtgtc atgtgtgaaa ataataattt       2820
aatggtttgt aagttattct tctatttgat gttttaagtc acttgttta tatttttcct       2880 gtgatggatt tatattatga attttttatat aaattatttt tttttccttt ttcaaggttg     2940
catttcaata ccagtcatat taaccatttt cgaactctac ttcttttttat gacatagatt    3000 ttgaagcatt tttctgtgac cccactcaca attaggattc atttggtaca aacaactagc    3060
ccgtggcgag tcaactatga gggcatatat atatatattt ttttttccat ttagacttga    3120
actatcctac tttatggtat taatcgagcc atgtttcaac ttagaatttt cattcatatt      3180
attagaggct ttctagattg aatttgttaa attttatggg tctaattcca cactttatta     3240
tgactaggct tatgaggata tgctaggggt cttcttgacc ttcattggtc tgagatgtcc    3300
gttacggtca ggacctgcac tcagatcatg a                                    3331

<210> SEQ ID NO 5
<211> LENGTH: 1087
<212> TYPE: DNA
<213> ORGANISM: Capsicum annuum
<220> FEATURE:
<221> NAME/KEY: misc_feature
<222> LOCATION: (968)...(982)
<223> OTHER INFORMATION: UPA Box

<400> SEQUENCE: 5
atttcttcta tgtgccttgt gtccaaaaga tgtttcagaa gttcgcgttg ggaagttgtc      60
accctacgga atagcagcat taaggcacat cagagatttt tgggtgtta agtttgtcat      120 gaaacctgat gcctccacag gaactgtcaa tctcatgtgt cttggctctg gttttcagaa    180
tttatccaga aaagtatcat gataaattaa tggtgtctgt gtttggtggc ttagagtgac    240
ggctagatca acatctttgg gatgccttgt ggagtgaaat caagcatact ttatcatagg   300
cgaaattttt tgttgtggtt tgctgcttgt aatgagagag tgatatagga agcaaatgtg  360
gagatcacat ttgctcatct ccttgttgcg ttgaaacttt tggtgtcaag agttctaatt    420
cacatgtatt tgaagattcc tcatatgctg cttttgtttc taattatttt ttctagtaag  480
aaaacatttg ttcctgagtt tccaactaga aaaaatatc aagtaaaata gaattcaatc  540
atttccctta ccaacgcttg gtactgccaa ccgcaacaaa gaattaatgc aaaacaacag 600
tctattaata tcaacctaga ctaaactcct tagttttact ttgaaatgcg aatgatacat    660
gacacattag attgtacttg cttttacca cagatacaac gatacatttg tatatctttt    720
cccttatagc aaactctaat atatcatagt caagctaacg aaacttatgc aagggaaata   780
tgaaattagt atgcaagtaa actcaaagaa ctaatcattg aactgaaaga tcaatatatc   840
aaaaaaaaaa aaaaaacaat aaaaccgttt aaccgataga ttaaccatttt ctggttcagt   900 ttatgggtta accacaatt tgcacaccct ggttaaacaa tgaacacgtt tgcctgacca     960
attttattat ataaacctaa ccatcctcac aacttcaagt tatcatcccc tttctctttt   1020
```

```
ctcctcttgt tcttgtcacc cgctaaatct atcaaaacac aagtagtcct agttgcacat      1080
atatttc                                                                1087

<210> SEQ ID NO 6
<211> LENGTH: 344
<212> TYPE: DNA
<213> ORGANISM: Capsicum annuum
<220> FEATURE:
<221> NAME/KEY: misc_feature
<222> LOCATION: (225)...(239)
<223> OTHER INFORMATION: UPA Box

<400> SEQUENCE: 6
tcatagtcaa gctaacgaaa cttatgcaag ggaaatatga aattagtatg caagtaaact        60
caaagaacta atcattgaac tgaaagatca atatatcaaa aaaaaaaaaa aaacaataaa       120
accgtttaac cgatagatta accatttctg gttcagttta tgggttaaac cacaatttgc       180
acaccctggt taaacaatga acacgtttgc ctgaccaatt ttattatata aacctaacca       240
tcctcacaac ttcaagttat catccccttt ctcttttctc ctcttgttct tgtcacccgc       300
taaatctatc aaaacacaag tagtcctagt tgcacatata tttc                       344

<210> SEQ ID NO 7
<211> LENGTH: 166
<212> TYPE: DNA
<213> ORGANISM: Capsicum annuum
<220> FEATURE:
<221> NAME/KEY: misc_feature
<222> LOCATION: (47)...(61)
<223> OTHER INFORMATION: UPA Box

<400> SEQUENCE: 7
gcacaccctg gttaaacaat gaacacgttt gcctgaccaa ttttattata taacctaac        60 catcctcaca acttcaagtt atcatcccct ttctcttttc tcctcttgtt cttgtcaccc      120
gctaaatcta tcaaaacaca agtagtccta gttgcacata tatttc                    166

<210> SEQ ID NO 8
<211> LENGTH: 90
<212> TYPE: DNA
<213> ORGANISM: Capsicum annuum

<400> SEQUENCE: 8
agttatcatc cccttctct tttctcctct tgttcttgtc accgctaaa tctatcaaaa        60 cacaagtagt cctagttgca catatatttc                                       90

<210> SEQ ID NO 9
<211> LENGTH: 1029
<212> TYPE: DNA
<213> ORGANISM: Capsicum annuum
<220> FEATURE:
<221> NAME/KEY: CDS
<222> LOCATION: (1)...(1026)

<400> SEQUENCE: 9 atg atg aat cag aat tgc ttt aat tct tgt tca cct cta act gtt gat        48
Met Met Asn Gln Asn Cys Phe Asn Ser Cys Ser Pro Leu Thr Val Asp
1               5                   10                  15 gca ctt gaa cca aaa aaa tcc tct tgt gct gct aaa tgc ata caa gta        96
Ala Leu Glu Pro Lys Lys Ser Ser Cys Ala Ala Lys Cys Ile Gln Val
            20                  25                  30 aat ggt cct ctt att gtt gga gct ggc cct tca ggc ctg gct act gct       144
Asn Gly Pro Leu Ile Val Gly Ala Gly Pro Ser Gly Leu Ala Thr Ala
        35                  40                  45
```

```
gcc gtc ctt aag caa tac agt gtt ccg tat gta atc att gaa cgc gcg    192
Ala Val Leu Lys Gln Tyr Ser Val Pro Tyr Val Ile Ile Glu Arg Ala
    50              55                  60 gac tgc att gct tct ctg tgg caa cac aag acc tac gat cgg ctt agg    240
Asp Cys Ile Ala Ser Leu Trp Gln His Lys Thr Tyr Asp Arg Leu Arg
65              70                  75                  80 ctt aac gtg cca cga caa tac tgc gaa ttg cct ggc ttg cca ttt cca    288
Leu Asn Val Pro Arg Gln Tyr Cys Glu Leu Pro Gly Leu Pro Phe Pro
            85                  90                  95 cca gac ttt cca gag tat cca acc aaa aac caa ttc atc agc tac ctc    336
Pro Asp Phe Pro Glu Tyr Pro Thr Lys Asn Gln Phe Ile Ser Tyr Leu
                100                 105                 110 gta tct tat gca aag cat ttc gag atc aaa cca caa ctc aac gag tca    384
Val Ser Tyr Ala Lys His Phe Glu Ile Lys Pro Gln Leu Asn Glu Ser
            115                 120                 125 gta aac tta gct gga tat gat gag aca tgt ggt tta tgg aag gtg aaa    432
Val Asn Leu Ala Gly Tyr Asp Glu Thr Cys Gly Leu Trp Lys Val Lys
        130                 135                 140 aca gtt tct gaa atc aat ggt tca acc tct gaa tac atg tgt aag tgg    480
Thr Val Ser Glu Ile Asn Gly Ser Thr Ser Glu Tyr Met Cys Lys Trp
145                 150                 155                 160 ctt att gtg gcc aca gga gag aat gct gag atg ata gtg ccc gaa ttc    528
Leu Ile Val Ala Thr Gly Glu Asn Ala Glu Met Ile Val Pro Glu Phe
                165                 170                 175 gaa gga ttg caa gat ttt ggt ggc cag gtt att cat gct tgt gag tac    576
Glu Gly Leu Gln Asp Phe Gly Gly Gln Val Ile His Ala Cys Glu Tyr
            180                 185                 190 aag act ggg gaa tac tat act gga gaa aat gtg ctg gcg gtt ggc tgt    624
Lys Thr Gly Glu Tyr Tyr Thr Gly Glu Asn Val Leu Ala Val Gly Cys
        195                 200                 205 ggc aat tcc ggg atc gat atc tca ctt gat ctt tcc caa cat aat gca    672
Gly Asn Ser Gly Ile Asp Ile Ser Leu Asp Leu Ser Gln His Asn Ala
210                 215                 220 aat cca ttc atg gta gtt cga agc tcg gta cag ggt cgt aat ttc cct    720
Asn Pro Phe Met Val Val Arg Ser Ser Val Gln Gly Arg Asn Phe Pro
225                 230                 235                 240 gag gaa ata aac ata gtt cca gca atc aag aaa ttt act caa gga aaa    768
Glu Glu Ile Asn Ile Val Pro Ala Ile Lys Lys Phe Thr Gln Gly Lys
                245                 250                 255 gta gaa ttt gtt aat gga caa att cta gag atc gac tct gtt atc ttg    816
Val Glu Phe Val Asn Gly Gln Ile Leu Glu Ile Asp Ser Val Ile Leu
            260                 265                 270 gca act ggt tat acc agc aat gta act tct tgg tta atg gag agt gaa    864
Ala Thr Gly Tyr Thr Ser Asn Val Thr Ser Trp Leu Met Glu Ser Glu
        275                 280                 285 ttt ttt tca agg gag gga tgt cca aaa agc cca ttc cca aat ggt tgg    912
Phe Phe Ser Arg Glu Gly Cys Pro Lys Ser Pro Phe Pro Asn Gly Trp
290                 295                 300 aag ggg gag gat ggt ctc tat gca gtt gga ttt aca gga ata gga ctg    960
Lys Gly Glu Asp Gly Leu Tyr Ala Val Gly Phe Thr Gly Ile Gly Leu
305                 310                 315                 320 ttt ggt gct tct ata gat gcc act aat gtt gca caa gat att gcc aaa    1008
Phe Gly Ala Ser Ile Asp Ala Thr Asn Val Ala Gln Asp Ile Ala Lys
                325                 330                 335 att tgg aaa gaa caa atg tag                                        1029
Ile Trp Lys Glu Gln Met
        340
```

```
<210> SEQ ID NO 10
<211> LENGTH: 342
<212> TYPE: PRT
<213> ORGANISM: Capsicum annuum

<400> SEQUENCE: 10

Met Met Asn Gln Asn Cys Phe Asn Ser Cys Ser Pro Leu Thr Val Asp
 1               5                  10                  15

Ala Leu Glu Pro Lys Lys Ser Ser Cys Ala Ala Lys Cys Ile Gln Val
             20                  25                  30

Asn Gly Pro Leu Ile Val Gly Ala Gly Pro Ser Gly Leu Ala Thr Ala
         35                  40                  45

Ala Val Leu Lys Gln Tyr Ser Val Pro Tyr Val Ile Ile Glu Arg Ala
 50                  55                  60

Asp Cys Ile Ala Ser Leu Trp Gln His Lys Thr Tyr Asp Arg Leu Arg
 65                  70                  75                  80

Leu Asn Val Pro Arg Gln Tyr Cys Glu Leu Pro Gly Leu Pro Phe Pro
                 85                  90                  95

Pro Asp Phe Pro Glu Tyr Pro Thr Lys Asn Gln Phe Ile Ser Tyr Leu
            100                 105                 110

Val Ser Tyr Ala Lys His Phe Glu Ile Lys Pro Gln Leu Asn Glu Ser
        115                 120                 125

Val Asn Leu Ala Gly Tyr Asp Glu Thr Cys Gly Leu Trp Lys Val Lys
    130                 135                 140

Thr Val Ser Glu Ile Asn Gly Ser Thr Ser Glu Tyr Met Cys Lys Trp
145                 150                 155                 160

Leu Ile Val Ala Thr Gly Glu Asn Ala Glu Met Ile Val Pro Glu Phe
                165                 170                 175

Glu Gly Leu Gln Asp Phe Gly Gly Gln Val Ile His Ala Cys Glu Tyr
            180                 185                 190

Lys Thr Gly Glu Tyr Tyr Thr Gly Glu Asn Val Leu Ala Val Gly Cys
        195                 200                 205

Gly Asn Ser Gly Ile Asp Ile Ser Leu Asp Leu Ser Gln His Asn Ala
    210                 215                 220

Asn Pro Phe Met Val Val Arg Ser Ser Val Gln Gly Arg Asn Phe Pro
225                 230                 235                 240

Glu Glu Ile Asn Ile Val Pro Ala Ile Lys Lys Phe Thr Gln Gly Lys
                245                 250                 255

Val Glu Phe Val Asn Gly Gln Ile Leu Glu Ile Asp Ser Val Ile Leu
            260                 265                 270

Ala Thr Gly Tyr Thr Ser Asn Val Thr Ser Trp Leu Met Glu Ser Glu
        275                 280                 285

Phe Phe Ser Arg Glu Gly Cys Pro Lys Ser Pro Phe Pro Asn Gly Trp
    290                 295                 300

Lys Gly Glu Asp Gly Leu Tyr Ala Val Gly Phe Thr Gly Ile Gly Leu
305                 310                 315                 320

Phe Gly Ala Ser Ile Asp Ala Thr Asn Val Ala Gln Asp Ile Ala Lys
                325                 330                 335

Ile Trp Lys Glu Gln Met
            340

<210> SEQ ID NO 11
<211> LENGTH: 1026
<212> TYPE: DNA
<213> ORGANISM: Capsicum annuum
```

<400> SEQUENCE: 11

```
atgatgaatc agaattgctt taattcttgt tcacctctaa ctgttgatgc acttgaacca          60
aaaaaatcct cttgtgctgc taaatgcata caagtaaatg gtcctcttat tgttggagct         120
ggcccttcag gcctggctac tgctgccgtc cttaagcaat acagtgttcc gtatgtaatc         180
attgaacgcg cggactgcat tgcttctctg tggcaacaca agacctacga tcggcttagg         240
cttaacgtgc cacgacaata ctgcgaattg cctggcttgc catttccacc agactttcca         300
gagtatccaa ccaaaaacca attcatcagc tacctcgtat cttatgcaaa gcatttcgag         360
atcaaaccac aactcaacga gtcagtaaac ttagctggat atgatgagac atgtggttta         420
tggaaggtga aaacagtttc tgaaatcaat ggttcaacct ctgaatacat gtgtaagtgg         480
cttattgtgg ccacaggaga gaatgctgag atgatagtgc ccgaattcga aggattgcaa         540
gattttggtg ccaggttat tcatgcttgt gagtacaaga ctggggaata ctatactgga          600
gaaaatgtgc tggcggttgg ctgtggcaat tccgggatcg atatctcact tgatctttcc         660
caacataatg caaatccatt catggtagtt cgaagctcgg tacagggtcg taatttccct         720
gaggaaataa acatagttcc agcaatcaag aaatttactc aaggaaaagt agaatttgtt         780
aatggacaaa ttctagagat cgactctgtt atcttggcaa ctggttatac cagcaatgta         840
acttcttggt taatggagag tgaattttt tcaaggagg gatgtccaaa aagcccattc           900
ccaaatggtt ggaagggga ggatggtctc tatgcagttg gatttacagg aataggactg          960
tttggtgctt ctatagatgc cactaatgtt gcacaagata ttgccaaaat ttggaaagaa        1020
caaatg                                                                    1026
```

<210> SEQ ID NO 12
<211> LENGTH: 3344
<212> TYPE: DNA
<213> ORGANISM: Capsicum annuum
<220> FEATURE:
<221> NAME/KEY: misc_feature
<222> LOCATION: (979)...(991)
<223> OTHER INFORMATION: 13 nucleotide insertion (relative to Bs3 promoter)
<220> FEATURE:
<221> NAME/KEY: misc_feature
<222> LOCATION: (968)...(995)
<223> OTHER INFORMATION: UPA Box wtih 13 nucleotide insertion from 979 to 991

<400> SEQUENCE: 12

```
atttcttcta tgtgccttgt gtccaaaaga tgtttcagaa gttcgcgttg ggaagttgtc          60
accctacgga atagcagcat taaggcacat cagagatttt ttgggtgtta agtttgtcat         120
gaaacctgat gcctccacag gaactgtcaa tctcatgtgt cttggctctg gttttcagaa         180
tttatccaga aaagtatcat gataaattaa tggtgtctgt gtttggtggc ttagagtgac         240
ggctagatca acatctttgg gatgccttgt ggagtgaaat caagcatact ttatcatagg         300
cgaaattttt tgttgtggtt tgctgcttgt aatgagagag tgatatagga agcaaatgtg         360
gagatcacat ttgctcatct ccttgttgcg ttgaaacttt tggtgtcaag agttctaatt         420
cacatgtatt tgaagattcc tcatatgctg cttttgtttc taattatttt ttctagtaag         480
aaaacatttg ttcctgagtt tccaactaga aaaaaatatc aagtaaaata gaattcaatc         540
atttccctta ccaacgcttg gtactgccaa ccgcaacaaa gaattaatgc aaaacaacag         600
tctattaata tcaacctaga ctaaactcct tagttttact ttgaaatgcg aatgatacat         660
gacacattag attgtacttg ctttttacca cagatacaac gatacatttg tatatctttt         720
```

-continued

```
cccttatagc aaactctaat atatcatagt caagctaacg aaacttatgc aagggaaata    780
tgaaattagt atgcaagtaa actcaaagaa ctaatcattg aactgaaaga tcaatatatc    840
aaaaaaaaaa aaaaaacaat aaaaccgttt aaccgataga ttaaccattt ctggttcagt    900
ttatgggtta aaccacaatt tgcacaccct ggttaaacaa tgaacacgtt tgcctgacca    960
attttattat ataaacctct ctattccact aaaccatcct cacaacttca agttatcatc   1020
ccctttctct tttctcctct tgttcttgtc acccgctaaa tctatcaaaa cacaagtagt   1080
cctagttgca catatatttc atgatgaatc agaattgctt taattcttgt tcacctctaa   1140
ctgttgatgc acttgaacca aaaaaatcct cttgtgctgc taaatgcata caagtaaatg   1200
gtcctcttat tgttggagct ggcccttcag gcctggctac tgctgccgtc cttaagcaat   1260
acagtgttcc gtatgtaatc attgaacgcg cggactgcat tgcttctctg tggcaacaca   1320
agacctacga tcggcttagg cttaacgtgc cacgacaata ctgcgaattg cctggcttgc   1380
catttccacc agacttttcca gagtatccaa ccaaaaacca attcatcagc tacctcgtat   1440
cttatgcaaa gcatttcgag atcaaaccac aactcaacga gtcagtaaac ttagctggat   1500
atgatgagac atgtggttta tggaaggtga aaacagtttc tgaaatcaat ggttcaacct   1560
ctgaatacat gtgtaagtgg cttattgtgg ccacaggaga gaatgctgag atgatagtgc   1620
ccgaattcga aggattgcaa gattttggtg gccaggttat tcatgcttgt gagtacaaga   1680
ctggggaata ctatactgga gaaaatgtgc tggcggttgg ctgtggcaat tccgggatcg   1740
atatctcact tgatctttcc caacataatg caaatccatt catggtagtt cgaagctcgg   1800
taagttttat attcaataag tattattttt caagtaacac tagaaagtga tcttgtatct   1860
ttcatttgct cgcatgaata tattatattc acacatgaat gatatcatct agttttgtta   1920
atctttcagg tacagggtcg taatttccct gaggaaataa acatagttcc agcaatcaag   1980
aaatttactc aaggaaaagt agaatttgtt aatggacaaa ttctagagat cgactctgtt   2040
atcttggcaa ctggttatac cagcaatgta acttcttggt taatggtaag gaaatacaca   2100
agttttattt ctatgcctaa ttaaattggt gtttaatcat aaattatata tagtactaag   2160
tatgataaaa gctccttcaa ctataaagga tgatttagtc aaatgaactc ttaatgaatg   2220
tagtaattat ttatggattc ttgttacatt catgtaagtt ggtatctcat tatcctgtgg   2280
attctttcct ttgagttatt aattagttag aattcactat aaccgtcttt tttctttttac   2340 cctttcctca taccttttg ttcttttgat aactcgaact cacaatctta agattgggaa   2400 taagggctc tttaccatct gagcaacttt ctctcgttct ataatagccc tcttcgaaat   2460
ttggtctaat gagaatttta ctgatacagg agagtgaatt ttttcaagg gagggatgtc   2520 caaaaagccc attcccaaat ggttggaagg gggaggatgg tctctatgca gttggattta   2580
caggaatagg actgtttggt gcttctatag atgccactaa tgttgcacaa gatattgcca   2640
aaatttggaa agaacaaatg tagcacaaga atcataatca atctgttgga tgcatgccat   2700
ggagaagaag caagttactt ttctcatgtc aagaaaataa gatttttttt tttcttcctg   2760
taatattact gggattggat attctcccag ttgccttttg tttgatttgt gtcatgtgtg   2820
aaaataataa tttaatggtt tgtaagttat tcttctattt gatgttttaa gtcacttgtt   2880 ttatatttt cctgtgatgg atttatatta tgaattttta tataaattat ttttttttcc   2940
tttttcaagg ttgcatttca ataccagtca tattaaccat tttcgaactc tacttctttt   3000
tatgacatag attttgaagc attttctgt gaccccactc acaattagga ttcatttggt   3060
acaaacaact agcccgtggc gagtcaacta tgagggcata tatatatata tttttttttc   3120
```

-continued

```
catttagact tgaactatcc tactttatgg tattaatcga gccatgtttc aacttagaat    3180
tttcattcat attattagag gctttctaga ttgaatttgt taaattttat gggtctaatt    3240
ccacacttta ttatgactag gcttatgagg atatgctagg ggtcttcttg accttcattg    3300
gtctgagatg tccgttacgg tcaggacctg cactcagatc atga                    3344
```

<210> SEQ ID NO 13
<211> LENGTH: 1100
<212> TYPE: DNA
<213> ORGANISM: Capsicum annuum
<220> FEATURE:
<221> NAME/KEY: misc_feature
<222> LOCATION: (979)...(991)
<223> OTHER INFORMATION: 13 bp insertion (relative to Bs3 promoter)
<220> FEATURE:
<221> NAME/KEY: misc_feature
<222> LOCATION: (968)...(995)
<223> OTHER INFORMATION: UPA Box wtih 13 nucleotide insertion from 979
      to 991

<400> SEQUENCE: 13

```
atttcttcta tgtgccttgt gtccaaaaga tgtttcagaa gttcgcgttg ggaagttgtc      60
accctacgga atagcagcat taaggcacat cagagatttt ttgggtgtta agtttgtcat     120
gaaacctgat gcctccacag gaactgtcaa tctcatgtgt cttggctctg gttttcagaa     180
tttatccaga aaagtatcat gataaattaa tggtgtctgt gtttggtggc ttagagtgac     240
ggctagatca acatctttgg gatgccttgt ggagtgaaat caagcatact ttatcatagg     300
cgaaattttt tgttgtggtt tgctgcttgt aatgagagag tgatatagga agcaaatgtg     360
gagatcacat ttgctcatct ccttgttgcg ttgaaacttt tggtgtcaag agttctaatt     420
cacatgtatt tgaagattcc tcatatgctg cttttgtttc taattatttt ttctagtaag     480
aaaacatttg ttcctgagtt tccaactaga aaaaaatatc aagtaaaata gaattcaatc     540
atttccctta ccaacgcttg gtactgccaa ccgcaacaaa gaattaatgc aaaacaacag     600
tctattaata tcaacctaga ctaaactcct tagttttact ttgaaatgcg aatgatacat     660
gacacattag attgtacttg cttttttacca cagatacaac gatacatttg tatatctttt     720
cccttatagc aaactctaat atatcatagt caagctaacg aaacttatgc aagggaaata     780
tgaaattagt atgcaagtaa actcaaagaa ctaatcattg aactgaaaga tcaatatatc     840 aaaaaaaaa aaaaaacaat aaaaccgttt aaccgataga ttaaccatttt ctggttcagt     900 ttatgggtta aaccacaatt tgcacaccct ggttaaacaa tgaacacgtt tgcctgacca     960 atttttattat ataaacctct ctattccact aaaccatcct cacaacttca agttatcatc    1020 cccttctct tttctcctct tgttcttgtc acccgctaaa tctatcaaaa cacaagtagt    1080
cctagttgca catatatttc                                                1100
```

<210> SEQ ID NO 14
<211> LENGTH: 357
<212> TYPE: DNA
<213> ORGANISM: Capsicum annuum
<220> FEATURE:
<221> NAME/KEY: misc_feature
<222> LOCATION: (236)...(248)
<223> OTHER INFORMATION: 13 bp insertion (relative to Bs3 promoter)
<220> FEATURE:
<221> NAME/KEY: misc_feature
<222> LOCATION: (225)...(252)
<223> OTHER INFORMATION: UPA Box wtih 13 nucleotide insertion from 236
      to 248

-continued

```
<400> SEQUENCE: 14
tcatagtcaa gctaacgaaa cttatgcaag ggaaatatga aattagtatg caagtaaact    60
caaagaacta atcattgaac tgaaagatca atatatcaaa aaaaaaaaaa aaacaataaa   120
accgtttaac cgatagatta accatttctg gttcagttta tgggttaaac cacaatttgc   180
acaccctggt taaacaatga acacgtttgc ctgaccaatt ttattatata aacctctcta   240
ttccactaaa ccatcctcac aacttcaagt tatcatcccc tttctctttt ctcctcttgt   300
tcttgtcacc cgctaaatct atcaaaacac aagtagtcct agttgcacat atatttc     357
```

```
<210> SEQ ID NO 15
<211> LENGTH: 179
<212> TYPE: DNA
<213> ORGANISM: Capsicum annuum
<220> FEATURE:
<221> NAME/KEY: misc_feature
<222> LOCATION: (58)...(70)
<223> OTHER INFORMATION: 13 bp insertion (relative to Bs3 promoter)
<220> FEATURE:
<221> NAME/KEY: misc_feature
<222> LOCATION: (47)...(74)
<223> OTHER INFORMATION: UPA Box wtih 13 nucleotide insertion from 58
      to 70

<400> SEQUENCE: 15
gcacaccctg gttaaacaat gaacacgttt gcctgaccaa ttttattata taaacctctc    60
tattccacta aaccatcctc acaacttcaa gttatcatcc cctttctctt ttctcctctt   120
gttcttgtca cccgctaaat ctatcaaaac acaagtagtc ctagttgcac atatatttc   179
```

```
<210> SEQ ID NO 16
<211> LENGTH: 90
<212> TYPE: DNA
<213> ORGANISM: Capsicum annuum

<400> SEQUENCE: 16
agttatcatc cctttctctt tttctcctct tgttcttgtc acccgctaaa tctatcaaaa    60
cacaagtagt cctagttgca catatatttc                                     90
```

```
<210> SEQ ID NO 17
<211> LENGTH: 14
<212> TYPE: DNA
<213> ORGANISM: Capsicum annuum
<220> FEATURE:
<221> NAME/KEY: misc_feature
<222> LOCATION: (1)...(14)
<223> OTHER INFORMATION: UPA Box - Consensus Sequence
<220> FEATURE:
<221> NAME/KEY: misc_feature
<222> LOCATION: 11, 12
<223> OTHER INFORMATION: n = A,T,C or G

<400> SEQUENCE: 17
tatataaacc nncc                                                      14
```

```
<210> SEQ ID NO 18
<211> LENGTH: 30
<212> TYPE: DNA
<213> ORGANISM: Artificial Sequence
<220> FEATURE:
<223> OTHER INFORMATION: PCR Primer A1-fwd-PR

<400> SEQUENCE: 18
ctacggaata gcagcattaa ggcacatcag                                     30
```

```
<210> SEQ ID NO 19
<211> LENGTH: 26
<212> TYPE: DNA
<213> ORGANISM: Artificial Sequence
<220> FEATURE:
<223> OTHER INFORMATION: PCR Primer B5-rev-PR

<400> SEQUENCE: 19
catacggaac actgtattgc ttaagg                                        26

<210> SEQ ID NO 20
<211> LENGTH: 32
<212> TYPE: DNA
<213> ORGANISM: Artificial Sequence
<220> FEATURE:
<223> OTHER INFORMATION: PCR Primer final-entry-01-fwd

<400> SEQUENCE: 20
atgatgaatc agaattgctt taattcttgt tc                                 32

<210> SEQ ID NO 21
<211> LENGTH: 30
<212> TYPE: DNA
<213> ORGANISM: Artificial Sequence
<220> FEATURE:
<223> OTHER INFORMATION: PCR Primer final-entry-02-rev

<400> SEQUENCE: 21
catttgttct ttccaaattt tggcaatatc                                    30

<210> SEQ ID NO 22
<211> LENGTH: 30
<212> TYPE: DNA
<213> ORGANISM: Artificial Sequence
<220> FEATURE:
<223> OTHER INFORMATION: PCR Primer Cand-7-01-fwd

<400> SEQUENCE: 22
atgaatcaga attgctttaa ttcttgttca                                    30

<210> SEQ ID NO 23
<211> LENGTH: 28
<212> TYPE: DNA
<213> ORGANISM: Artificial Sequence
<220> FEATURE:
<223> OTHER INFORMATION: PCR Primer Cand-7-01-rev

<400> SEQUENCE: 23
tgattcttgt gctacatttg ttctttcc                                      28

<210> SEQ ID NO 24
<211> LENGTH: 20
<212> TYPE: DNA
<213> ORGANISM: Artificial Sequence
<220> FEATURE:
<223> OTHER INFORMATION: PCR Primer RS-EFrt-F1

<400> SEQUENCE: 24
agtcaactac cactggtcac                                               20

<210> SEQ ID NO 25
<211> LENGTH: 21
<212> TYPE: DNA
<213> ORGANISM: Artificial Sequence
<220> FEATURE:
<223> OTHER INFORMATION: PCR Primer RS-EFrt-R1
```

```
<400> SEQUENCE: 25
gtgcagtagt acttagtggt c                                                    21
```

BS3 RESISTANCE GENE AND METHODS OF USE

CROSS-REFERENCE TO RELATED APPLICATIONS

This application claims the benefit of U.S. Provisional Application No. 60/976,017, filed Sep. 28, 2007, which is hereby incorporated herein in its entirety by reference.

BACKGROUND OF THE INVENTION

Plants are hosts to thousands of infectious diseases caused by a vast array of phytopathogenic fungi, bacteria, viruses, oomycetes and nematodes. Plants recognize and resist many invading phytopathogens by inducing a rapid defense response. Recognition is often due to the interaction between a dominant or semi-dominant resistance (R) gene product in the plant and a corresponding dominant avirulence (Avr) gene product expressed by the invading phytopathogen. R-gene triggered resistance often results in a programmed cell-death, that has been termed the hypersensitive response (HR). The HR is believed to constrain spread of the pathogen.

How R gene products mediate perception of the corresponding Avr proteins is mostly unclear. It has been proposed that phytopathogen Avr products function as ligands, and that plant R products function as receptors. In this receptor-ligand model binding of the Avr product to a corresponding R product in the plant initiates the chain of events within the plant that produces HR leads to disease resistance. In an alternate model the R protein perceives the action rather than the structure of the Avr protein. In this model the Avr protein is believed to modify a plant target protein (pathogenicity target) in order to promote pathogen virulence. The modification of the pathogenicity protein is detected by the matching R protein and triggers a defense response. Experimental evidence suggests that some R proteins act as Avr receptors while others detect the activity of the Avr protein.

The production of transgenic plants carrying a heterologous gene sequence is now routinely practiced by plant molecular biologists. Methods for incorporating an isolated gene sequence into an expression cassette, producing plant transformation vectors, and transforming many types of plants are well known. Examples of the production of transgenic plants having modified characteristics as a result of the introduction of a heterologous transgene include: U.S. Pat. No. 5,719,046 to Guerineau (production of herbicide resistant plants by introduction of bacterial dihydropteroate synthase gene); U.S. Pat. No. 5,231,020 to Jorgensen (modification of flavenoids in plants); U.S. Pat. No. 5,583,021 to Dougherty (production of virus resistant plants); and U.S. Pat. No. 5,767,372 to De Greve and U.S. Pat. No. 5,500,365 to Fischoff (production of insect resistant plants by introducing *Bacillus thuringiensis* genes).

In conjunction with such techniques, the isolation of plant R genes has similarly permitted the production of plants having enhanced resistance to certain pathogens. Since the cloning of the first R gene, Pto from tomato, which confers resistance to *Pseudomonas syringae* pv. tomato (Martin et al. (1993) *Science* 262: 1432-1436), a number of other R genes have been reported (Hammond-Kosack & Jones (1997) *Ann. Rev. Plant Physiol. Plant Mol. Biol.* 48:575-607). A number of these genes have been used to introduce the encoded resistance characteristic into plant lines that were previously susceptible to the corresponding pathogen. For example, U.S. Pat. No. 5,571,706 describes the introduction of the Ngene into tobacco lines that are susceptible to Tobacco Mosaic Virus (TMV) in order to produce TMV-resistant tobacco plants. WO 95/28423 describes the creation of transgenic plants carrying the Rps2 gene from *Arabidopsis thaliana*, as a means of creating resistance to bacterial pathogens including *Pseudomonas syringae*, and WO 98/02545 describes the introduction of the Prf gene into plants to obtain broad-spectrum pathogen resistance.

Bacterial spot disease of tomato and pepper, caused by the phytopathogenic bacterium *Xanthomonas campestris* pv. *vesicatoria* (Xcv), can be devastating to commercial production of these crops in areas of the world with high humidity and heavy rainfall. While control of Xcv in commercial agriculture is based largely on the application of pesticides, genetic resistance to bacterial spot disease has been described in both tomato and pepper (Cook and Stall (1963) *Phytopathology* 53: 1060-1062; Cook and Guevara (1984) *Plant Dis.* 68: 329-330; Kim and Hartman (1985) *Plant Dis.* 69: 233-235; Jones and Scott (1986) *Plant Dis.* 70: 337-339). Of the two hosts, genetic resistance in pepper has been better characterized. Several single loci (Bs), Bs2, and Bs3) that confer resistance in a "gene-for-gene" manner have been identified (Hibberd et al. (1987) *Phytopathology* 77: 1304-1307). Moreover, the corresponding avirulence genes (avrBs1, avrBs2, and avrBs3) have been cloned from Xcv (Swanson et al. (1988) *Mol Plant-Microbe Interact.* 1:5-9; Minsavage et al. (1990) *Mol. Plant-Microbe Interact.* 3: 41-47). Genetic and molecular characterization of these avirulence genes has provided a great deal of information concerning the interaction between Xcv and pepper (Kearney et al. (1988) *Nature* 332: 541-543; Kearney and Staskawicz (1990) *Nature* 346: 385-386; Herbers et al. (1992) *Nature* 356: 172-174; Van der Ackerveken et al. (1992) *Plant J.* 2: 359-366). More recently, the Bs3 gene of pepper has been isolated and sequenced (U.S. Pat. No. 6,262,343)

Xcv employs a type III secretion (T3S) system to inject an arsenal of about 20 effector proteins into the host cytoplasm that collectively promote virulence (Thieme et al. (2005) *J. Bacteriol.* 187:7254). R protein mediated defense in response to Xcv effector proteins is typically accompanied by a programmed cell death response referred to as the hypersensitive response (HR). AvrBs3 is one Avr protein that R proteins recognize and is a member of a *Xanthomonas* family of highly conserved proteins (Schornack et al. (2006) *J. Plant Physiol.* 163:256). The central region of AvrBs3 consists of 17.5 tandem near-perfect 34-amino-acid (aa) repeat units that determine avirulence specificity (Herbers et al. (1992) *Nature* 356: 172). AvrBs3 contains also nuclear localization signals (NLSs) and an acidic transcriptional activation domain (AD) (Szurek et al. (2001) *Plant J.* 26:523; Szurek et al. (2002) *Mol. Microbiol.* 46:13), similar to eukaryotic transcription factors, and induces host gene transcription (Marois et al. (2002) *Mol Plant-Microbe Interact.* 15:637-646). Mutations in the NLS or AD of AvrBs3 abolish pathogen recognition by the matching pepper R gene Bs3 (Szurek et al. (2001) *Plant J.* 26:523; Van den Ackerveken et al. (1996) *Cell* 87:1307) suggesting that recognition involves transcriptional activation of host genes.

The isolation to the Bs3 gene from pepper would provide researchers with the opportunity to further study this recognition process while providing an R gene that can be used to produce transgenic plants having increased resistance to phytopathogens.

BRIEF SUMMARY OF THE INVENTION

The present invention provides an isolated resistance (R) gene, the Bs3 gene from pepper (*Capsicum annuum*). The Bs3 gene is known to confer upon a plant resistance to the bacterial pathogen, *Xanthomonas campestris* pv. *vesicatoria*. As disclosed hereinbelow, transient co-expression of the Bs3 and avrBs3 genes in *Nicotiana benthamiana* leaves triggered the hypersensitive response (HR) in the leaves. In addition, the invention provides as second allele of the Bs3 gene, referred to as the Bs3-E allele, which triggers HR when co-expressed in *N. benthamiana* leaves with AvrBs3-derivative, AvrBs3Δrep16.

Thus, the invention provides isolated nucleic acid molecules comprising nucleotide sequences of two alleles of the Bs3 gene. Such nucleic acid molecules include both cDNA sequences and genomic sequences comprising full-length, coding sequences. Both alleles encode amino acid sequences that are homologous to the amino acid sequences of known flavin-dependent monooxygenases.

The invention further provides methods for increasing the resistance of a plant to a plant pathogen. Such methods involve transforming a plant with a nucleotide molecule of the present invention comprising a nucleotide sequence that encodes a Bs3 protein and an operably linked promoter that drives expression in a plant. Such plants have increased resistance to a plant pathogen.

The invention further provides isolated nucleic acid molecules comprising promoter sequences of the Bs3 gene. Such isolated nucleic acid molecules can be operably linked to a gene of interest for expression of the gene in a plant. Thus, the invention provides methods for expressing or increasing the expression of a protein or RNA of interest in a plant involving transforming a plant with a polynucleotide construct that comprises a promoter sequence of the invention operably linked to a gene of interest that encodes the protein or RNA of interest.

Additionally provided are plants, plant parts, seeds, plant cells and other non-human host cells transformed with the isolated nucleic acid molecules of the present invention and the proteins or polypeptides encoded by the coding sequences of the present invention.

BRIEF DESCRIPTION OF THE DRAWINGS

FIG. 1A. Recognition specificity of the Bs3 allele from ECW-30R. The Bs3 gene and/or avr genes were expressed transiently in *N. benthamiana* leaves via *A. tumefaciens* ($OD_{600}$=0.8). Dashed lines mark the inoculated areas. Four days after infiltration the leaves were cleared to visualize the hypersensitive response (dark areas)

FIG. 1B. Bs3-E and/or avr genes were transiently expressed in *N. benthamiana* leaves FIG. 1C. The relationship between domain structure and activity of AvrBs3, AvrBs3-derivatives and AvrBs4. +/− indicates presence/absence of the hypersensitive response (HR) in *N. benthamiana* upon co-expression of the pepper Bs3 or Bs3-E allele, respectively. For details, see FIG. 1A. White- and grey-boxed areas in the central part of the protein represent the repeat region of AvrBs3 and AvrBs4, respectively. AD refers to the C-terminal acidic transcriptional activation domain.

FIG. 1D. Gene structure of the ECW-30R Bs3 and the ECW Bs3-E alleles. Exons, introns, untranslated- and promoter regions are displayed to scale as white, black, grey and hatched boxes, respectively. The length of these elements (in base pairs) is indicated within the boxes. Differences between the Bs3 alleles are marked in boldface. A 13-bp insertion in the Bs3-E promoter relative to the Bs3 promoter is underlined. Nucleotide positions of the promoter and exon 3-polymorphisms are relative to the transcriptional and translational start sites, respectively. Amino-acids encoded by the polymorphic region in exon 3 are depicted above and below the nucleotide sequences. The portions of the ECW-30R Bs3 and ECW Bs3-E alleles shown in FIG. 1D correspond to SEQ ID NOS: 26 and 27, respectively.

FIG. 2. Chimeras containing the promoter (arrow) of the Bs3 allele (white) and the coding region (box) of the Bs3-E allele (black) or the reciprocal combination (right side of the leaf) were expressed together with avrBs3 and derivatives as indicated. Asterisks (*) mark an area in which only *A. tumefaciens* delivering the chimeric -constructs was infiltrated. Dashed lines mark the inoculated areas. Four days after inoculation leaves were cleared to visualize the hypersensitive response (dark areas).

FIG. 3. Semi-quantitative reverse transcription-polymerase chain reaction on cDNA of non-infected and Xcv-infected pepper ECW-30R (Bs3) and ECW (Bs3-E) leaves 24 hours after infection. The avrBs3-like genes that are expressed in the given Xcv strains are indicated (in parentheses). Elongation factor 1a (EF1a) was amplified as a control.

FIG. 4A. Electrophoretic mobility shift assay (EMSA) probes derived from Bs3 and Bs3-E promoter sequences (SEQ ID NOS: 28 and 29, respectively) Numbering is relative to the transcriptional start site. The 13 bp-insertion in the Bs3-E promoter is indicated in boldface. The position of biotin-labeled DNA fragments are indicated by lines above and below the promoter sequences. Probes I and II correspond to Bs3 and Bs3-E promoters, respectively, whereas probe III corresponds to an identical region in both promoters.

FIG. 4B. EMSA with AvrBs3 and Bs3- or Bs3-E-derived probes in a 6% non-denaturing polyacrylamide gel. Protein amounts are in fmol. Positions of the bound and free probe are indicated on the left.

FIG. 4C. EMSA competition experiment between AvrBs3 and different amounts (in fmol) of a non-labeled competitor probe.

FIG. 4D. Chromatin immunoprecipitation was conducted with AvrBs3-specific antibodies on extracts from ECW-30R (Bs3) and ECW (Bs3-E) plants that were infected with Xcv wild-type (WT avrBs3) strains or an isogenic type III secretion-deficient Xcv mutant strain (ΔhrcVavrBs3). Leaves were harvested 12 hours after inoculation. Semi-quantitative PCR with 32, 34 and 36 cycles was conducted before immunoprecipitation (input) or on immunoprecipitated material (IP). ECW-30R (Bs3) and ECW (Bs3-E) derived PCR products differ in size due to a 13-bp insertion in the Bs3-E promoter.

FIG. 5. Nucleotide and predicted amino acid sequences of the pepper Bs3 cDNA (SEQ ID NOS: 30 and 2, respectively). Nucleotide sequence was obtained by RT-PCR and RACE (rapid amplification of cDNA ends) performed on RNA from pepper cultivar ECW-30R. RNA was isolated from leaves that were inoculated with avrBs3-expressing Xcv. The translational stop codon is marked by an asterisk (*). Positions of introns identified by comparison with the genomic sequence are indicated by triangles. A guanine nucleotide present in cultivar ECW-30R that is replaced by thymidine in cultivar ECW (underlined) causes a leucine to phenylalanine change in the predicted ECW protein. Sequence motifs that are characteristic of Flavin monooxygenases (FMOs) are boxed in gray. Conserved residues in these motifs are shown in bold type. I, FAD binding motif (GXGXXG; SEQ ID NO: 40); II, FMO-identifying sequence motif (FXGXXXHXXX[Y/F]; SEQ ID NO: 41); III, NADPH-binding domain (GXGXX[G/A]; SEQ ID NO: 42) and IV, "FATGY" domain ([F/L]ATGY; SEQ ID NO: 43).

FIG. 6. Alignment of the predicted pepper Bs3 protein (SEQ ID NO: 2) to representative FMOs. The location of the conserved residues of the FAD-binding domain (GXGXXG; SEQ ID NO: 40), the FMO-identifying sequence motif (FXGXXXHXXX[Y/F]; SEQ ID NO: 41), the NADPH-binding domain (GXGXX[G/A]; SEQ ID NO: 42) and the conserved FATGY motif ([L/F]ATGY; SEQ ID NO: 43) are marked by asterisks (*). Names of proteins from *A. thaliana* (At YUCCA01 and At FMO1, SEQ ID NOS: 31 and 32, respectively), *Homo sapiens* (Hs FMO1, SEQ ID NO: 33), and *Saccharomyces cerevisiae* (Sc FMO1, SEQ ID NO: 34) are given along with their accession numbers (in parentheses). Alignments were constructed with ClustalW. Identical amino acids (white text on black background) and similar amino acids present in ≧50% of sequences (on grey background) were shaded using Boxshade. Dashes (–) indicate gaps.

Figure 7:
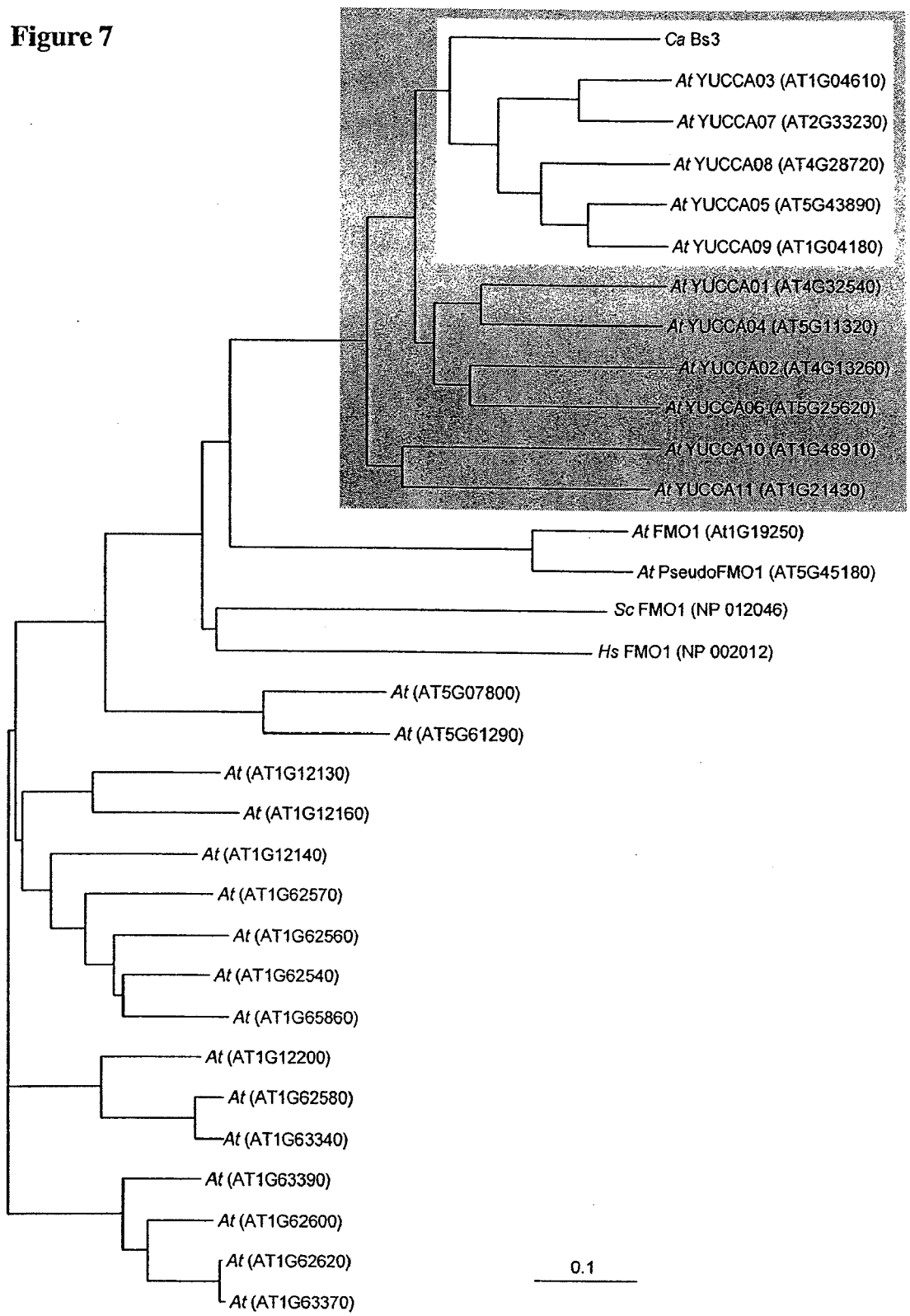

FIG. 7. A phylogenetic tree containing all predicted FMOs from *A. thaliana* (At), *S. cerevisiae* (Sc), human (Hs) and the predicted pepper (Ca) Bs3 protein. Names of proteins are given with their accession numbers (in parentheses). A monophyletic group that contains the predicted Bs3 protein and *Arabidopsis* YUCCA-like proteins is boxed in grey. A white box marks the most closely Bs3-related YUCCA proteins (see also FIG. 8). The branch lengths of the tree are proportional to divergence. The 0.1 scale represents 10% change. The amino acid sequences were aligned with ClustalW and the phylogenetic tree displayed with TreeView.

Figure 8:
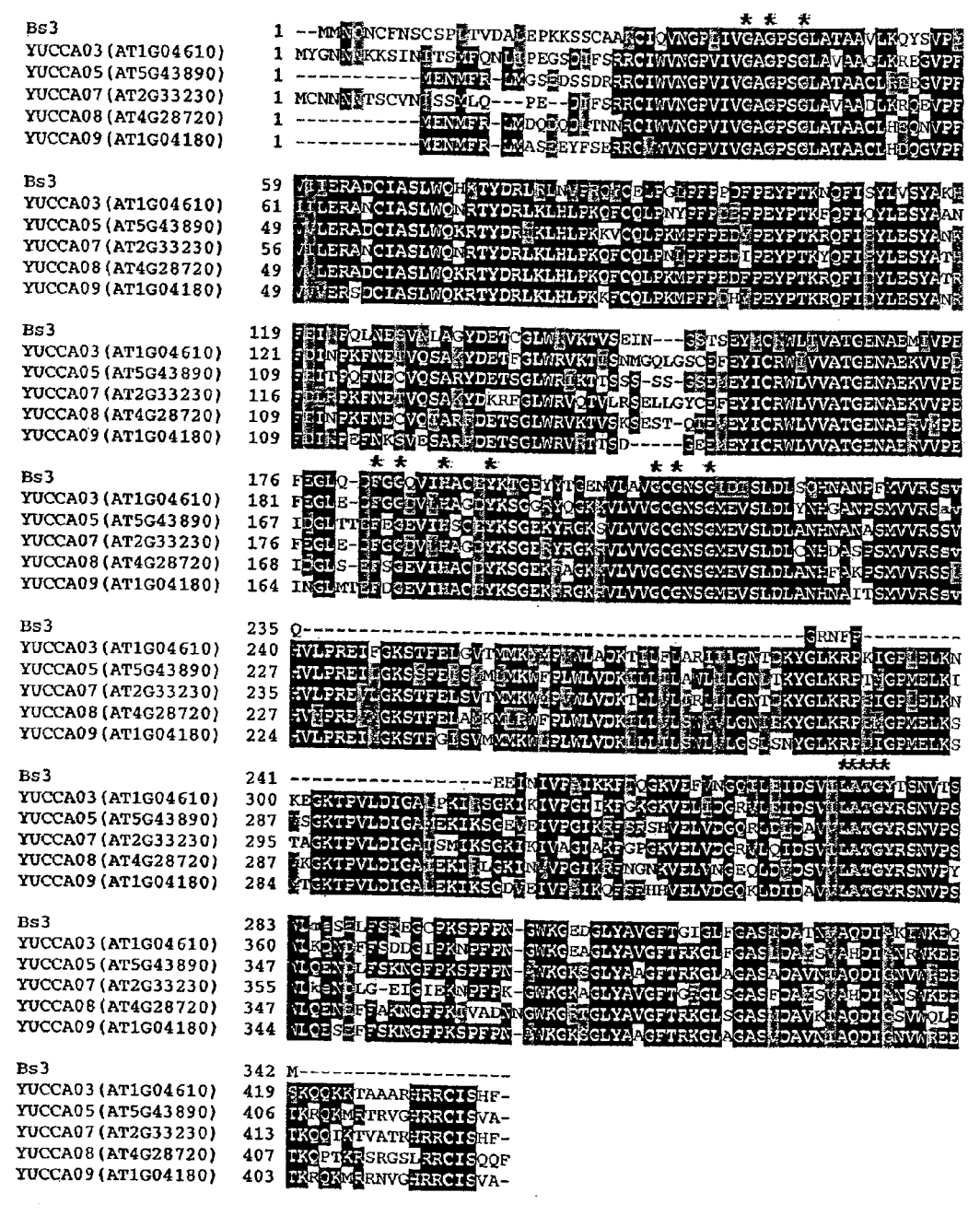

FIG. 8. The predicted Bs3 protein (SEQ ID NO: 2) and YUCCA-like proteins from *Arabidopsis* (YUCCA03, YUCCA05, YUCCA07, YUCCA08, and YUCCA09, SEQ ID NOS: 35-39, respectively) are structurally diverse. Alignment of YUCCA-like proteins from *Arabidopsis* that are closely related to the predicted Bs3 protein. A stretch of 72 residues is conserved in YUCCA-like *Arabidopsis* proteins, but is absent from the predicted Bs3 protein (begins at residue 240 of YUCCA03). The location of the conserved residues of the FAD-binding domain (GXGXXG; SEQ ID NO: 40), the FMO-identifying sequence motif (FXGXXXHXXX[Y/F]; SEQ ID NO: 41), the NADPH-binding domain (GXGXX[G/A]; SEQ ID NO: 42) and the conserved FATGY motif ([L/F]ATGY; SEQ ID NO: 43) are marked are marked by asterisks (*). Amino acids that are located at the exon-exon junctions of the corresponding genes are marked in lowercase green. Names of proteins are given with their accession numbers (in parentheses). Alignments were constructed with ClustalW. Identical amino acids (white text on black background) and 50% similar amino acids (white on grey background) were shaded using Boxshade. A dash (-) indicates a gap.

Figure 9:
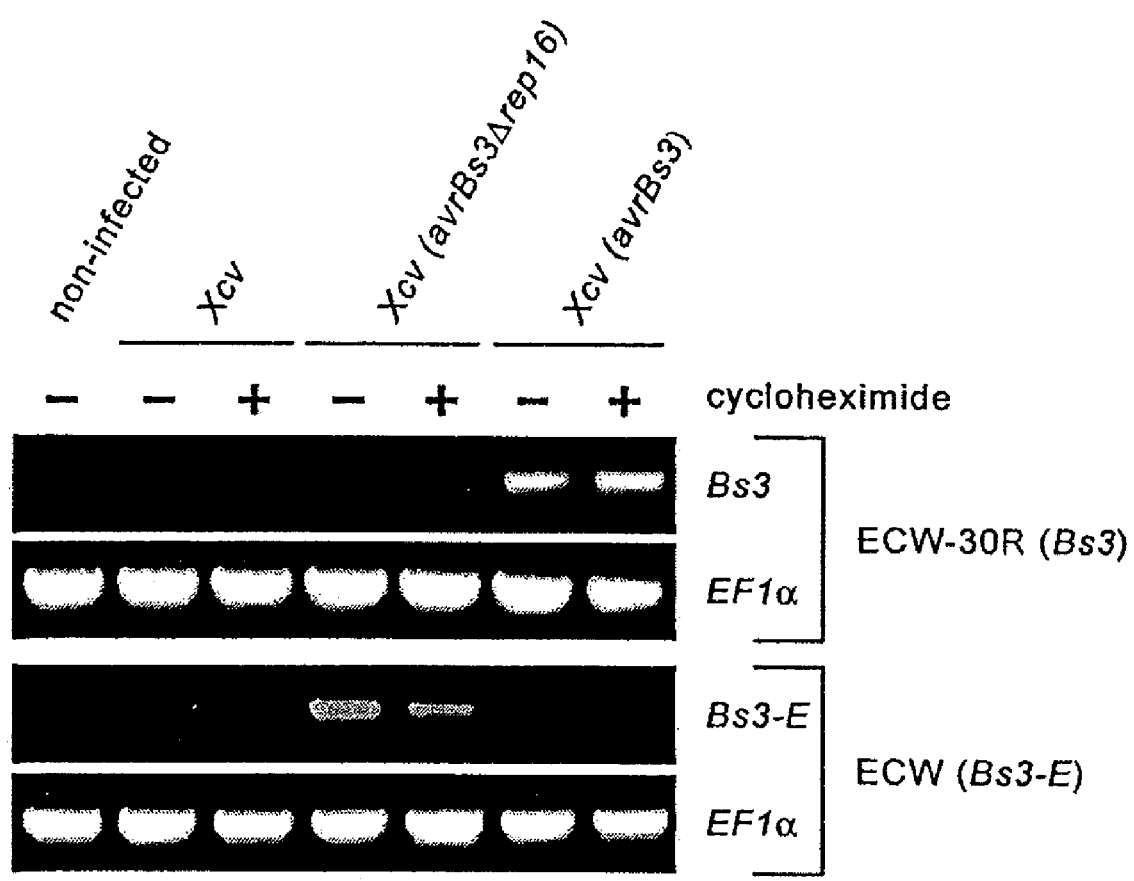

FIG. 9. Semi-quantitative reverse transcription-polymerase chain reaction was carried out on cDNA of non-infected and Xcv-infected pepper ECW-30R (Bs3) and ECW (Bs3-E) leaves 24 hours after infection. The avrBs3-like genes that are expressed in the given Xcv strains are indicated (in parentheses). Inoculations were carried out in the presence (+) or absence (–) of the eukaryotic protein synthesis inhibitor cycloheximide. Elongation factor 1a (EF1a) was amplified as a control.

Figure 10:
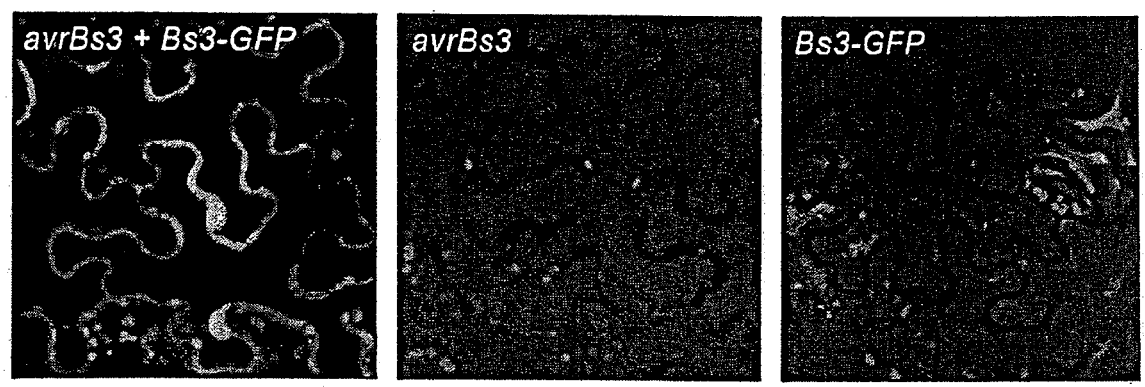

FIG. 10. Confocal imaging of GFP-tagged Bs3 was conducted two days after *A. tumefaciens* transient transformation of *N. benthamiana*. Bs3-GFP and avrBs3 are under transcriptional control of the Bs3 and the Cauliflower mosaic virus 35S promoter, respectively.

Figure 11:
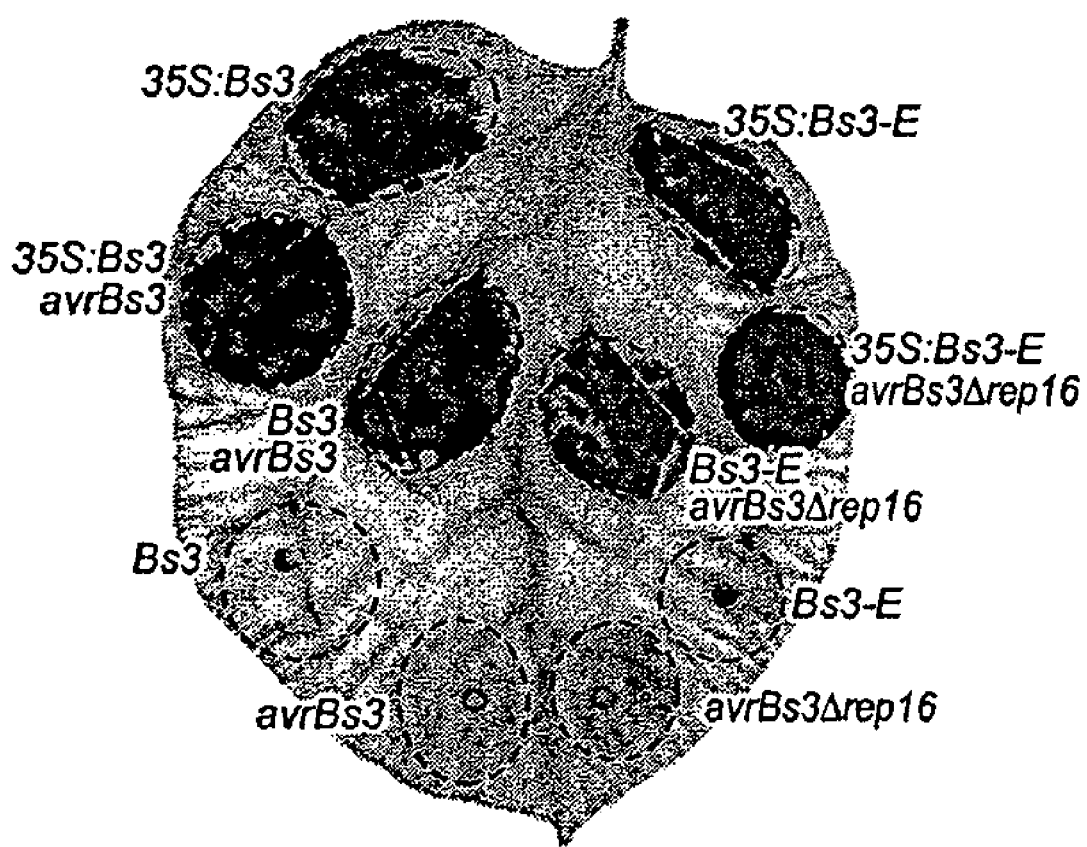

FIG. 11. Constitutive expression of the Bs3 and Bs3-E alleles triggers an Avr-independent HR. The coding regions of Bs3 and Bs3-E were expressed under the control of their own promoter (Bs3 and Bs3-E) or under control of the Cauliflower mosaic virus 35S promoter (35S:Bs3 and 35S:Bs3-E). The Bs3 alleles were expressed alone or together with the depicted avr genes. The genes were delivered into *N. benthamiana* leaves via *A. tumefaciens* transient transformation ($OD_{600}$=0.8). Four days after infiltration the leaves were cleared to visualize the hypersensitive response (dark areas).

FIG. 12A. GFP, GFP-fusion construct or an empty T-DNA (control) were transformed in *N. benthamiana* leaves by *A. tumefaciens*. Bs3 and the depicted Bs3 mutants are under transcriptional control of the Bs3 promoter (Bs3) or the Cauliflower mosaic virus 35S promoter (35S:Bs3). Bs3 was expressed either alone or together with avrBs3 as indicated. Dashed lines mark the inoculated areas. Four days after infiltration the leaves were cleared to visualize the hypersensitive response (dark areas).

FIG. 12B. Protein extracts from *N. benthamiana* leaves 40 hours after infiltration with the indicated *A. tumefaciens* strains. Proteins were separated by SDS-PAGE and analyzed by immunoblot using a GFP-specific antibody. Molecular masses are given on the right in kilodalton (kDa). Arrowheads indicate the expected size of GFP and the Bs3-GFP fusion protein.

Figure 13:
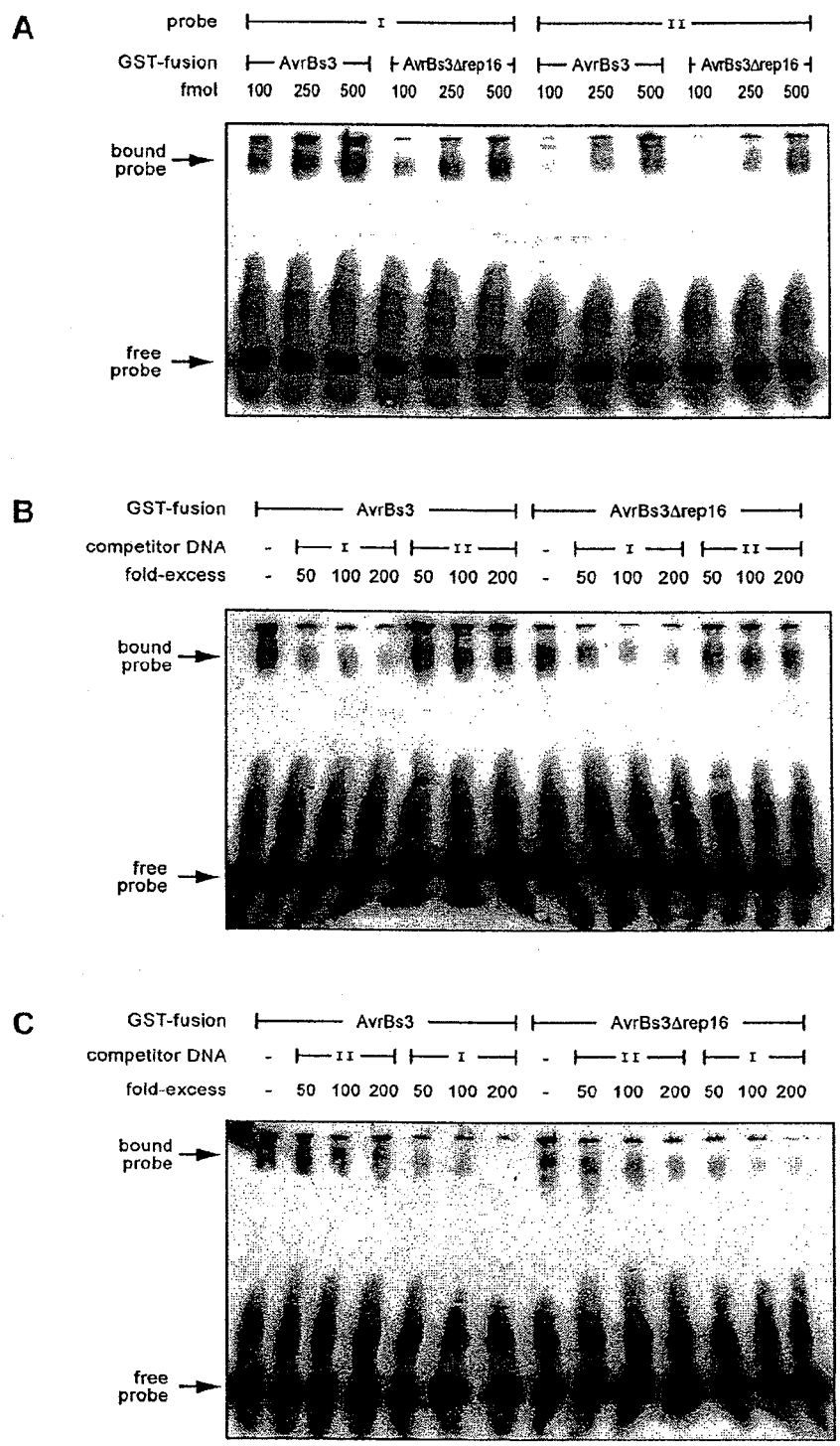

FIG. 13A. Electrophoretic mobility shift assay (EMSA) with AvrBs3 and AvrBs3Drep16. Protein amounts are given in fmol. The nucleotide sequences of DNA probe I and II are displayed in FIG. 4A. Positions of the bound and free probe are indicated by arrows on the left hand panel.

FIG. 13B. EMSA competition assay with Bs3-derived probe DNA.

FIG. 13C. Competition assay with Bs3-E-derived probe DNA.

Figure 14:
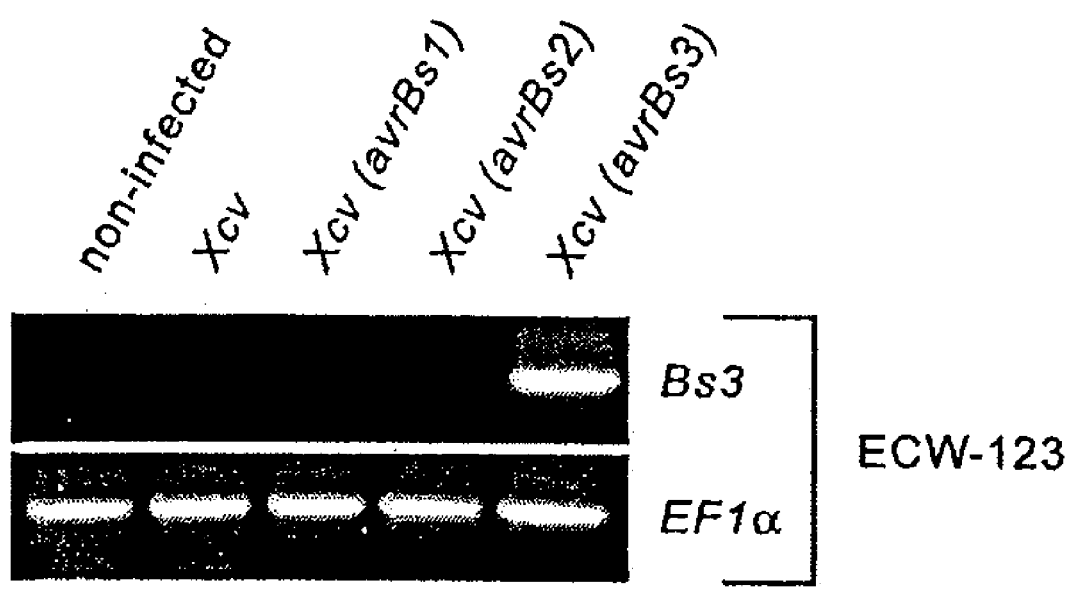

FIG. 14. RT-PCR of non-inoculated and Xcv-inoculated leaves harvested 10 hours after Xcv infection of the pepper cultivar ECW-123R (contains the R genes Bs1, Bs2 and Bs3). The avr genes that are expressed in the given Xcv strains are indicated. Elongation factor 1a (EF1a) expression was used to standardize the Bs3 transcript levels in each sample.

SEQUENCE LISTING

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleic acid sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth the full-length coding sequence of the Bs3 allele of the Bs3 gene.

SEQ ID NO: 2 sets forth the Bs3 amino acid sequence that is encoded by SEQ ID NO: 1.

SEQ ID NO: 3 sets forth the full-length coding sequence of the Bs3 allele of the Bs3 gene minus the stop codon. Nucleotides 1-1026 of SEQ ID NO: 3 correspond to nucleotides 1-1026 of SEQ ID NO: 1. If desired, a stop codon can be added to the 3' end of the nucleotide sequence of SEQ ID NO: 3 or any other coding sequence that lacks a stop codon. Such stop codons include, for example, TAA, TAG, and TGA.

SEQ ID NO: 4 sets forth the genomic sequence of the Bs3 allele of the Bs3 gene.

SEQ ID NO: 5 sets forth the nucleotide sequence of the promoter of the Bs3 allele of the Bs3 gene and corresponds to nucleotides 1-1087 of SEQ ID NO: 4.

SEQ ID NO: 6 sets forth a 344 bp fragment of the promoter of the Bs3 allele of the Bs3 gene. This fragment consists of the final 344 bp of the promoter sequence set forth in SEQ ID NO: 5.

SEQ ID NO: 7 sets forth a 166 bp fragment of the promoter of the Bs3 allele of the Bs3 gene. This fragment consists of the final 166 bp of the promoter sequence set forth in SEQ ID NO: 5.

SEQ ID NO: 8 sets forth a 90 bp fragment of the promoter of the Bs3 allele of the Bs3 gene. This fragment consists of the final 90 bp of the promoter sequence set forth in SEQ ID NO: 5.

SEQ ID NO: 9 sets forth the full-length coding sequence of the Bs3-E allele of the Bs3 gene.

SEQ ID NO: 10 sets forth the Bs3-E amino acid sequence that is encoded by SEQ ID NO: 9.

SEQ ID NO: 11 sets forth the full-length coding sequence of the Bs3-E allele of the Bs3 gene minus the stop codon. Nucleotides 1-1026 of SEQ ID NO: 11 correspond to nucleotides 1-1026 of SEQ ID NO: 9. If desired, a stop codon can be added to the 3' end of the nucleotide sequence of SEQ ID NO: 3 or any other coding sequence that lacks a stop codon. Such stop codons include, for example, TAA, TAG, and TGA.

SEQ ID NO: 12 sets forth the genomic sequence of the Bs3-E allele of the Bs3 gene.

SEQ ID NO: 13 sets forth the nucleotide sequence of the promoter of the Bs3-E allele of the Bs3 gene and corresponds to nucleotides 1-1100 of SEQ ID NO: 12.

SEQ ID NO: 14 sets forth a 357 bp fragment of the promoter of the Bs3-E allele of the Bs3 gene. This fragment consists of the final 357 bp of the promoter sequence set forth in SEQ ID NO: 13.

SEQ ID NO: 15 sets forth a 179 bp fragment of the promoter of the Bs3-E allele of the Bs3 gene. This fragment consists of the final 179 bp of the promoter sequence set forth in SEQ ID NO: 13.

SEQ ID NO: 16 sets forth a 90 bp fragment of the promoter of the Bs3-E allele of the Bs3 gene. This fragment consists of the final 90 bp of the promoter sequence set forth in SEQ ID NO: 13.

SEQ ID NO: 17 sets forth the consensus sequence for the UPA Box. The "nn" at positions 11-12 can be either two (nn) or three (nnn) nucleotides.

SEQ ID NO: 18 sets forth the nucleotide sequence of PCR primer designated as A1-fwd-PR.

SEQ ID NO: 19 sets forth the nucleotide sequence of PCR primer designated as B5-rev-PR.

SEQ ID NO: 20 sets forth the nucleotide sequence of PCR primer designated as final-entry-01-fwd.

SEQ ID NO: 21 sets forth the nucleotide sequence of PCR primer designated as final-entry-02-rev.

SEQ ID NO: 22 sets forth the nucleotide sequence of PCR primer designated as Cand-7-01-fwd.

SEQ ID NO: 23 sets forth the nucleotide sequence of PCR primer designated as Cand-7-01-rev.

SEQ ID NO: 24 sets forth the nucleotide sequence of PCR primer designated as RS-EFrt-F1.

SEQ ID NO: 25 sets forth the nucleotide sequence of PCR primer designated as RS-EFrt-R1.

SEQ ID NO: 26 sets forth the nucleotide sequence of portions of the ECW-30R Bs3 allele.

SEQ ID NO: 27 sets forth the nucleotide sequence of portions of the ECW Bs3-E allele.

SEQ ID NO: 28 sets forth the nucleotide sequence of the Bs3 promoter from which probes were designed for use in electrophoretic mobility shift assays (EMSAs).

SEQ ID NO: 29 sets forth the nucleotide sequence of the Bs3-E promoter from which probes were designed for use in electrophoretic mobility shift assays (EMSAs).

SEQ ID NO: 30 sets forth the nucleotide sequence of the pepper Bs3 cDNA. Nucleotides 60-1088 of SEQ ID NO: 30 correspond to SEQ ID NO: 1.

SEQ ID NO: 31 sets forth the At YUCCA01 (AT4G32540) amino acid sequence.

SEQ ID NO: 32 sets forth the At FMO1 (AT1G19250) amino acid sequence.

SEQ ID NO: 33 sets forth the Hs FMO1 (NP002012) amino acid sequence.

SEQ ID NO: 34 sets forth the Sc FMO1 (NP012046) amino acid sequence.

SEQ ID NO: 35 sets forth the At YUCCA03 (AT1G04610) amino acid sequence.

SEQ ID NO: 36 sets forth the At YUCCA05 (AT5G43890) amino acid sequence.

SEQ ID NO: 37 sets forth the At YUCCA07 (AT2G33230) amino acid sequence.

SEQ ID NO: 38 sets forth the At YUCCA08 (AT4G28720) amino acid sequence.

SEQ ID NO: 39 sets forth the At YUCCA09 (AT1G04180) amino acid sequence.

SEQ ID NO: 40 sets forth the amino acid sequence of the FAD-binding domain.

SEQ ID NO: 41 sets forth the amino acid sequence of the FMO-identifying motif.

SEQ ID NO: 42 sets forth the amino acid sequence of the NADPH-binding domain.

SEQ ID NO: 43 sets forth the amino acid sequence of the FATGY motif.

DETAILED DESCRIPTION OF THE INVENTION

The present invention discloses the isolation and sequencing of two alleles of an R gene, the Bs3 gene from pepper. The Bs3 gene is known to confer resistance to the bacterial pathogen, *Xanthomonas campestris* pv. *vesicatoria* (Xcv). Thus, the present invention provides isolated nucleic acid molecules comprising Bs3 nucleotide sequences. Such nucleotide sequences find use in the production of transformed plants with increased resistance to pathogens, particularly bacterial pathogens, more particularly *Xanthomonas* spp., even move particularly *Xanthomonas campestris*, and most particularly Xcv. Accordingly, the present invention provides methods for enhancing or increasing the resistance of a plant to a plant pathogen.

This present invention provides isolated Bs3 polypeptides and Bs3 nucleic acid molecules, including cDNA sequences, gene sequences, and promoter sequences. The prototypical Bs3 sequences are the pepper sequences, and the invention provides for the use of these sequences to produce transgenic plants, such as pepper and tomato plants, having enhanced resistance to diseases cause by *Xanthomonas campestris*, such as bacterial spot disease.

The nucleotide sequence of the Bs3 allele of the pepper Bs3 gene is set forth in SEQ ID NO: 4. This nucleotide sequence comprises 2 introns and 3 exons and a UPA box in the promoter region. The cDNA sequence is set forth in SEQ ID NO: 1. The open reading frame of the Bs3 gene encodes the 342 amino acid Bs3 protein. The amino acid sequence of the Bs3 protein is set forth in SEQ ID NO: 2. The nucleotide sequence of the 1087 bp, the promoter of the Bs3 allele is set forth in SEQ ID NO: 5. The nucleotide sequences of 5' truncations of the promoter comprising 344, 166, and 90 bps are set forth in SEQ ID NOS: 6-8, respectively.

The nucleotide sequence of the Bs3-E allele of the pepper Bs3 gene is set forth in SEQ ID NO: 12. Like the Bs3 allele, this nucleotide sequence comprises 2 introns and 3 exons and a UPA box in the promoter region. The cDNA sequence is set forth in SEQ ID NO: 9. The open reading frame encodes the 342 amino acid Bs3-E protein. The amino acid sequence of the Bs3-E protein is set forth in SEQ ID NO: 10. The Bs3-E promoter is set forth in SEQ ID NO: 13. The nucleotide sequences of 5' truncations of the promoter comprising 357, 179, and 90 bps are set forth in SEQ ID NOS: 14-16, respectively.

Throughout the present disclosure, references to the "Bs3 gene" are intended to encompass both alleles of the Bs3 gene unless stated otherwise or readily apparent from the context. Similarly, reference to the "Bs3 protein" is intended to encompass the proteins encoded by both alleles of the Bs3 gene unless stated otherwise or readily apparent from the context.

In one aspect, the present invention provides isolated nucleic acid molecules comprising nucleotide sequences encoding the Bs3 protein. Such isolated nucleic acid molecules find use in methods for expressing, or increasing the expression of, the Bs3 protein in a plant, plant part, plant cell, or other non-human host cell. Given that the Bs3 protein is homologous to known FMOs, expressing or increasing the expression of the Bs3 protein in the plant, plant part, plant cell, or other non-human host cell will not only lead to an increase in the level of the Bs3 protein but likely also cause an increase in FMO activity in the plant, plant part, plant cell, or other non-human host cell.

For expression of the Bs3 protein in a plant or plant cells, the methods of the invention involve transforming a plant with a polynucleotide of the present invention that encodes the Bs3 protein. Such an isolated nucleotide molecule can be operably linked to a promoter that drives expression in a plant cell. Any promoter known in the art can be used in the methods of the invention including, but not limited to, the pathogen-inducible promoters, wound-inducible promoters, tissue-preferred promoters, and chemical-regulated promoters. The choice of promoter will depend on the desired timing and location of expression in the transformed plant or other factors. In one embodiment of the invention, the native Bs3 promoter—either in its native genomic linkage to the downstream Bs3 gene sequences or as part of a recombinant nucleic acid molecule further comprising a Bs3 coding sequence—is employed to increase the expression of the Bs3 protein in a plant in response to the presence of Xcv on the plant or the introduction of the AvrBs3 protein to the plant or co-expression of a nucleic acid molecule encoding AvrBs3 in the plant. It is recognized that such an increase in the Bs3 protein in the leaves of a plant will trigger HR in the leaves. In a preferred embodiment of the invention, the promoter is the Bs3 promoter comprising the nucleotide sequence set forth in SEQ ID NO: 5 or one of the truncated Bs3 promoters comprising the nucleotide sequences set forth in SEQ ID NOS: 6 and 7.

The invention further provides methods for increasing the resistance of a plant to at least one plant pathogen. The methods involve transforming at least one plant cell with a nucleotide molecule of the invention encoding the Bs3 protein. The methods can further involve regenerating the transformed plant cell into a transformed plant. In one embodiment of the invention, the isolated nucleotide molecule comprises the Bs3 gene sequence set forth in SEQ ID NO: 4. It is recognized that the nucleotide sequence of the Bs3 gene that is set forth in SEQ ID NO: 4 comprises the promoter of the Bs3 gene, and therefore, no additional promoter is required for expression in a plant of interest. It is further recognized that not all of the 1087 bp that is 5' of the translation start in SEQ ID NO: 4 is required to direct pathogen-inducible (or AvrBs3-inducible) gene expression in a plant. It is further recognized that the Bs3 promoter is functional for plant pathogen-inducible gene expression when the first 783 or 921 bp from the 5' end of SEQ ID NO: 4 is omitted from a nucleotide molecule comprising the nucleotide sequence set forth in SEQ ID NO:4. In other embodiments, an isolated nucleic acid molecule of the invention is operably linked to a promoter that is capable of driving gene expression in a plant. In such embodiments, the isolated nucleotide molecule encodes the Bs3 protein. Preferably, the promoter is a pathogen-inducible promoter, particularly one the drives expression in response to a pathogen of interest or part or component thereof (e.g., an Avr protein). Preferred promoters include, for example, the Bs3 promoter set forth in SEQ ID NO: 5 and the truncations of the Bs3 promoter set forth in SEQ ID NOS: 6 and 7. Such preferred promoters comprise the Bs3 UPA box that corresponds to nucleotides 968-982 of SEQ ID NO: 5, nucleotides 225-239 of SEQ ID NO: 6, and nucleotides 47-61 of SEQ ID NO: 7.

Other preferred promoters include any functional fragments of the Bs3 promoter set forth in SEQ ID NO: 5 that comprise the Bs3 UPA box set forth in nucleotides 968-982 of SEQ ID NO: 5. Particularly preferred are those functional fragments of the Bs3 promoter that are truncations of the Bs3 promoter, particularly 5' truncations, including, but not limited to, the truncations of the Bs3 promoter set forth in SEQ ID NOS: 6 and 7. The present invention additionally encompasses the Bs3 UPA box comprising nucleotides 968-982 of SEQ ID NO: 5.

In addition to the Bs3 promoter and functional fragments thereof, the invention further provides the Bs3-E promoter and functional fragments thereof. The Bs3-E promoter and functional fragments thereof find use in the methods disclosed herein. The functional fragments of the Bs3-E promoter comprise promoter activity. Preferrably, such functional fragments are pathogen-inducible promoters. Such pathogen-inducible promoters are capably of driving or increasing the expression of an operably linked polynucleotide in response to a pathogen of interest or part or component thereof (e.g., an Avr protein). Preferred promoters include, for example, the Bs3-E promoter set forth in SEQ ID NO: 13 and the truncations of the Bs3-E promoter set forth in SEQ ID NOS: 14 and 15. Such preferred promoters comprise the Bs3-E UPA box that corresponds to nucleotides 968-995 of SEQ ID NO: 13, nucleotides 225-252 of SEQ ID NO: 14, and nucleotides 47-74 of SEQ ID NO: 15.

Other preferred promoters include any functional fragments of the Bs3-E promoter set forth in SEQ ID NO: 13 that comprise the Bs3-E UPA box set forth in nucleotides 968-995 of SEQ ID NO: 13. When compared to the Bs3 UPA box (TATATAAACCTAACC; nucleotides 968-982 of SEQ ID NO: 5), the Bs3-E UPA box has an insertion of 13 additional nucleotides (TATATAAACCTctctattccactaAACC; insertion lower case; nucleotides 968-995 of SEQ ID NO: 13) Particularly preferred are those functional fragments of the Bs3-E promoter that are truncations of the Bs3-E promoter, particularly 5' truncations, including, but not limited to the truncations of the Bs3-E promoter set forth in SEQ ID NOS: 14 and 15. The present invention additionally encompasses the Bs3-E UPA box comprising nucleotides 968-995 of SEQ ID NO: 13.

The methods for increasing the resistance of a plant to at least one plant pathogen find use in increasing or enhancing the resistance of plants, particularly agricultural or crop plants, to plant pathogens. The methods of the invention can be used with any plant species including monocots and dicots. Preferred plants include Solanaceous plants, such as, for example, pepper and tomato.

In a preferred embodiment of the methods for increasing the resistance of a plant to at least one plant pathogen, the plant pathogen is Xcv. However, the methods of the invention are not limited to the plant pathogen, Xcv. Other plant pathogens include, but are not limited to, other xanthomonads. By "xanthomonads" is intended bacterial species that are members of the genus *Xanthomonas*.

In other embodiments, the methods can involve additional R genes to increase plant resistance to a single plant pathogen or increase plant resistant to different plant pathogen. For example, a pepper plant comprising the Bs2 resistance gene can be transformed with an isolated nucleotide molecule encoding the Bs3 gene as described above to increase resistance to Xcv. Alternatively, the plant can be transformed with both the Bs2 and Bs3 genes either separately or as part of a single polynucleotide construct. The nucleotide sequences of the Bs2 have been previously disclosed. See, U.S. Pat. Nos. 6,262,343 and 6,762,285; each of which is herein incorporated by reference.

In another embodiment, the methods can involve transforming a plant with a pathogen-inducible promoter operably linked to a polynucleotide of the present invention that encodes the Bs3 protein. The invention does not depend on a particular pathogen-inducible promoter. Preferably, the pathogen-inducible promoter is one that directs very little or no expression of the operably linked Bs3 polynucleotide in the absence or the inducing pathogen or inducing part or component thereof. It is recognized that the by placing a Bs3 polynucleotide under the control of such a pathogen-inducible promoter, the expression of the Bs3 polynucleotide can be induced in plant in response to any pathogen or pathogens to which that promoter is responsive. It is further recognized expression in a plant of the Bs3 protein from such a Bs3 polynucleotide can induce cell death. In a preferred embodiment of the invention, expression of the Bs3 protein from a pathogen-inducible promoter that is active at the site, or in vicinity, of the pathogen attack on the plant causes cell death at the site, or in vicinity, of the pathogen attack and that such cell death inhibits or otherwise delays the development of plant disease.

The Bs3 coding sequences of the invention find further use in methods for causing cell death in a plant part of interest. Such a plant part of interest can be, for example, a plant cell or cell, a plant tissue, a plant organ, a seed, or part thereof. Expression of Bs3 coding sequence in plant part of interest leads to the production of the Bs3 protein, a flavin-dependent monooxygenase, which can cause the death of the plant part of interest. Such methods can be used, for example, to make a male sterile plant by expressing a Bs3 coding sequence under the direction of an operably linked promoter that drives gene expression in pollen cells or other cells or tissues that give rise to, or support, the growth and development of pollen, particularly male reproductive tissues. Such male sterile plants find use in the production of hybrid crop plants be reducing the need to remove male reproductive parts or organs from the maternal parent plant of the hybrid crop plant.

The methods for causing cell death in a plant part of interest involve transforming a plant cell with polynucleotide construct comprising a promoter that drives expression in a plant cell operably linked a Bs3 coding sequence of the present invention. Such a promoter directs expression of the Bs3 in the plant part of interest. Preferably, the promoter is one the directs expression little or no expression in plant cells or parts other than the plant part of interest where cell death is desired. The methods further involve regenerating the transformed plant cell into a transformed plant. In the transformed plant, cell death occurs in the plant part of interest upon expression of the Bs3 coding sequence of the present invention in the plant part of interest. Cell death can occur in all cells in the plant part of interest or can occur in a subset of cells within the plant part of interest or even in a single cell.

In another aspect, the invention provides isolated nucleic acid molecules comprising the nucleotide sequences of regions of the Bs3 gene that control or regulate gene expression in a plant, otherwise known as promoters. Such promoters find use in controlling the expression of the Bs3 gene or any other gene of interest in a plant, plant cell or plant part. It is recognized that the promoters of the invention are inducible promoters that direct little or no expression of operably linked nucleotide sequences in the absence of Xcv or the AvrBs3 but provide high-level expression in the presence of avrBs3-expressing Xcv. The promoters of the invention include those comprising the nucleotide sequences set forth SEQ ID NOS: 5-7 and 13-15, and fragments and variants thereof that comprise the pathogen-inducible promoter activity of the promoters comprising the nucleotide sequences set forth SEQ ID NOS: 5-7 and 13-15.

Thus, the invention further provides methods for expressing a gene of interest in a plant, plant part, or plant cell. The methods involve operably linking a promoter of the present invention to a gene of interest so as to produce a polynucleotide construct. Such genes of interest will depend on the desired outcome and can comprise nucleotide sequences that encode proteins and/or RNAs of interest. The methods further involve transforming at least one plant cell with the polynucleotide construct. The methods can additionally involve regenerating the transformed plant cell into a transformed plant. The gene of interest is expressed when the promoter is induced after exposing the plant, plant part, or plant cell to Xcv and/or AvrBs3. Based on studies of the expression of the Bs3 transcripts, it is expected the expression of the gene of interest will be detectable within about 6 hours after Xcv infection or treatment with AvrBs3, peak at about 12 hours after infection and remain at that level until about 24 hours after infection or treatment. Expression of the gene of interest can be determined by any method known in the art for measuring the expression of a gene at the RNA, protein, and/or metabolic (e.g., enzyme activity) levels. Methods of monitoring change in gene expression include, for example, Northern blotting, Western blotting, and enzyme assays.

By "gene of interest" is intended any nucleotide sequence that can be expressed when operable linked to a promoter. A gene of interest of the present invention may, but need not, encode a protein. Unless stated otherwise or readily apparent from the context, when a gene of interest of the present invention is said to be operably linked to a promoter of the invention, the gene of interest does not by itself comprise a functional promoter.

In another aspect, the present invention provides a method for expressing a gene in a plant, plant part, or plant cell. The method makes use of the ability of AvrBs3 to induce the expression of genes of interest operably linked to the Bs3 promoter and can be used to achieve high-level expression of the gene of interest in the plant, or part or cell thereof. The method involves a first polynucleotide construct and a second polynucleotide construct that can be linked on the same nucleic acid molecule or unlinked as two separate nucleic acid molecules. The first polynucleotide construct comprises a first promoter of the invention operably linked to the coding sequence of AvrBs3 (EMBL Accession X16130.1; GenBank Accession CAA34257). The second polynucleotide construct comprises a second promoter of the invention operably linked to a gene of interest. The first promoter can be any promoter that is capable of directing expression of a AvrBs3 coding sequence in a plant or part or cell thereof including, but not limited to, a constitutive promoter, a wound-inducible promoter, a pathogen-inducible promoter, a chemical-regulated promoter, a chemical-inducible promoter, a tissue-preferred promoter, and a Bs3 promoter of the present invention. The second promoter is a Bs3 promoter of the present invention. The method involves producing a transformed or transgenic plant that comprises both the first and second polynucleotide constructs.

In one embodiment of this method of the invention, the first promoter is a chemical-inducible promoter and the transformed plant comprises both the first and second polynucleotide constructions as described above. After such a transformed plant is first exposed to the chemical inducer, the increase in the expression of AvrBs3 coding sequences from the first construct will lead to production of AvrBs3 protein within cells of the plant and such AvrBs3 protein will induce the expression of the gene of interest in the second polynucleotide construct leading to high-level expression of gene product of the gene of interest. Such a gene product can be, for example, a protein or an RNA.

In another embodiment of this method of the invention, the first promoter is a Bs3 promoter of the invention, and the transformed plant comprises both the first and second polynucleotide constructions as described above. After such a transformed plant is first exposed to Xcv or AvrBs3, the increase in the expression of AvrBs3 coding sequences from the first construct will lead to production of AvrBs3 protein within cells of the plant and such AvrBs3 protein will induce further the expression of the gene of interest in the second polynucleotide construct leading to high-level expression of gene product of the gene of interest. Such a gene product can be, for example, a protein or an RNA.

A plant comprising both the first and second polynucleotide constructs can be produced by any method know in the art. For example, such a plant can be produced by the steps of (1) transforming a the plant cell with a single nucleic acid molecule comprising both constructs, or by co-transforming the cell with the first and second polynucleotide constructs, each on a separate nucleic acid molecule, and (2) regenerating a transformed plant that comprises both the first and second polynucleotide constructs. Alternatively, a first transformed plant can be produced that comprises the first polynucleotide construct. The second polynucleotide construct is introduced into a cell of the first transformed plant and a second transformed plant is regenerated therefrom which comprises both the first and second polynucleotide constructs. It is recognized that in such a sequential transformation, the second polynucleotide construct can be introduced into a plant cell to produce a first transformed plant followed by introduction of the first polynucleotide construct into a cell of the first plant and the subsequent production of a second transformed plant comprising both constructs. Another alternative involves sexual reproduction to combine the two constructs in a single plant. In this alternative, a first transformed plant that comprises the first polynucleotide construct is crossed to a second transformed plant that comprises the second polynucleotide construct and allowed to produce progeny or seeds that comprise both the first and second polynucleotide constructs.

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of a polynucleotides comprising coding sequences may encode protein fragments that retain biological activity of the native protein and hence flavin-dependent monooxygenases activity Fragments of polynucleotide comprising promoter sequences retain biological activity of the native promoter an hence retain Bs3 promoter activity. Alternatively, fragments of a polynucleotide that are useful as hybridization probes generally do not encode proteins that retain biological activity or do not retain promoter activity. Thus, fragments of a nucleotide sequence may range from at least about 20 nucleotides, about 50 nucleotides, about 100 nucleotides, and up to the full-length polynucleotide of the invention.

Unless stated otherwise or obvious from the context, "Bs3 promoter activity" is intended to mean the promoter activity of the Bs3 promoter or the Bs3-E promoter as disclosed herein. Likewise, unless stated otherwise or obvious from the context, the terms "Bs3 polynucleotide" and "Bs3 protein" (and similar terms) are intended to mean a polynucleotide of the Bs3 gene or the Bs3-E gene and the Bs3 protein or Bs3-E protein, respectively. Unless stated otherwise or obvious from the context, such terms also encompass variants and fragments of the Bs3 and Bs3-E nucleotide and amino acid sequences disclosed herein.

A fragment of a Bs3 polynucleotide that encodes a biologically active portion of a Bs3 protein of the invention will encode at least 15, 25, 30, 50, 100, 150, 200, 250, or 300 contiguous amino acids, or up to the total number of amino acids present in a full-length Bs3 protein of the invention (for example, 342 amino acids for both SEQ ID NOS: 2 and 10). Fragments of a Bs3 polynucleotide that are useful as hybridization probes or PCR primers generally need not encode a biologically active portion of a Bs3 protein or Bs3 promoter.

Thus, a fragment of a Bs3 polynucleotide may encode a biologically active portion of a Bs3 protein or Bs3 promoter, or it may be a fragment that can be used as a hybridization probe or PCR primer using methods disclosed below. A biologically active portion of a Bs3 protein can be prepared by isolating a portion of one of the Bs3 polynucleotides of the invention, expressing the encoded portion of the Bs3 protein (e.g., by recombinant expression in vitro), and assessing the activity of the encoded portion of the Bs3 protein. A biologically active portion of a Bs3 promoter can be prepared by isolating a portion of one of the Bs3 polynucleotides of the invention that comprises the Bs3 promoter, operably linking the portion of the promoter to nucleotide sequence (e.g. one that encodes a reporter gene) and assessing the activity of the promoter portion by monitoring the expression of the nucleotide sequence when the operably linked promoter portion and nucleotide sequence are introduced into a plant cell. Polynucleotides that are fragments of a Bs3 nucleotide sequence comprise at least 16, 20, 50, 75, 100, 125, 150, 175, 200, 250, 300, 350, 400, 450, 500, 550, 600, 650, 700, 800, 900, 1000, 1100, 1200, 1300, 1400, 1500, 2000, 2500, or 3000 contiguous nucleotides, or up to the number of nucleotides present in a full-length Bs3 polynucleotide disclosed herein (for example, 1029, 1026, 3331, 1087, 344, 166, 90, 1029, 1026, 3344, 1100, 357, 179, and 90 nucleotides for SEQ ID NOS: 1, 3-9, and 11-16, respectively).

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the Bs3 polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a Bs3 protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 2 and/or SEQ ID NO: 10 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein, that is, flavin-dependent monooxygenase activity as described herein. Such variants may result from, for example, genetic polymorphism or from human manipulation. Biologically active variants of a native Bs3 protein of the invention will have at least about 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the Bs3 proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass both naturally occurring proteins as well as variations and modified forms thereof. Such variants will continue to possess the desired Bs3 biological activity, particularly flavin-dependent monooxygenase activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by flavin-dependent monooxygenase activity assays. See, for example, Krueger et al. (2005). *Pharmacol. Ther.* 106, 357-387; herein incorporated by reference.

Variant polynucleotides and proteins also encompass sequences and proteins derived from a mutagenic and recombinogenic procedure such as DNA shuffling. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire Bs3 sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that have Bs3 promoter activity or encode for a Bs3 protein and which hybridize under stringent conditions to at least one of the Bs3 polynucleotides disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the Bs3 polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire Bs3 polynucleotide disclosed herein, or one or more portions thereof, may be used as a probe capable of specifically hybridizing to corresponding Bs3 polynucleotide and messenger RNAs. To achieve specific hybridization under a variety of conditions, such probes include sequences that are unique among Bs3 polynucleotide sequences and are optimally at least about 10 nucleotides in length, and most optimally at least about 20 nucleotides in length. Such probes may be used to amplify corresponding Bs3 polynucleotides from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

It is recognized that the polynucleotide molecules and proteins of the invention encompass polynucleotide molecules and proteins comprising a nucleotide or an amino acid sequence that is sufficiently identical to the nucleotide sequence of SEQ ID NOS: 1 and/or 3, or to the amino acid sequence of SEQ ID NO: 2. It is further recognized that the polynucleotide molecules and proteins of the invention encompass polynucleotide molecules and proteins comprising a nucleotide or an amino acid sequence that is sufficiently identical to the nucleotide sequence of SEQ ID NOS: 9 and/or 11, or to the amino acid sequence of SEQ ID NO: 10. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 90%, 95%, 96%, 97%, 98% or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264 modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention and using multiple alignment by mean of the algorithm Clustal W (Nucleic Acid Research, 22(22):4673-4680, 1994) using the program AlignX included in the software package Vector NTI Suite Version 7 (InforMax, Inc., Bethesda, MD, USA) using the default parameters; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by CLUSTALW (Version 1.83) using default parameters (available at the European Bioinformatics Institute website).

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The Bs3 polynucleotide of the invention comprising Bs3 protein coding sequences can be provided in expression cassettes for expression in the plant or other organism or non-human host cell of interest. The cassette will include 5' and 3' regulatory sequences operably linked to a Bs3 polynucleotide of the invention. "Operably linked" is intended to mean a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the Bs3 polynucleotide to be under the transcriptional regulation of the regulatory regions. The expression cassette may additionally contain selectable marker genes.

Likewise, the Bs3 promoter sequence of the invention can be provided in expression cassettes for expression in the plant or other organism or non-human host cell of interest. The cassette will include 3' regulatory sequences operably linked to a polynucleotide of gene of interest. The cassette may optionally additional 5' regulatory sequences. The Bs3 promoter sequence will be operably linked to the polynucleotide or gene of interest as described above. The cassette may additionally contain at least one additional gene to be cotransformed into the organism. Alternatively, the additional gene(s) can be provided on multiple expression cassettes. Such an expression cassette is provided with a plurality of restriction sites and/or recombination sites and may additionally contain selectable marker genes.

The expression cassette will include in the 5'-3' direction of transcription, a transcriptional and translational initiation region (i.e., a promoter), a Bs3 polynucleotide of the invention, and a transcriptional and translational termination region (i.e., termination region) functional in plants or other organism or non-human host cell. The regulatory regions (i.e., promoters, transcriptional regulatory regions, and translational termination regions) and/or the Bs3 polynucleotide of the invention may be native/analogous to the host cell or to each other. Alternatively, the regulatory regions and/or the Bs3 polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

Likewise, the Bs3 promoter sequence of the invention can be provided in expression cassettes for expression in the plant or other organism or non-human host cell of interest. The cassette will include 3' regulatory sequences operably linked to a polynucleotide of gene of interest. The cassette may optionally additional 5' regulatory sequences. The Bs3 promoter sequence will be operably linked to the polynucleotide or gene of interest as described above. The cassette may additionally contain at least one additional gene to be cotransformed into the organism. Alternatively, the additional gene(s) can be provided on multiple expression cassettes. Such an expression cassette is provided with a plurality of restriction sites and/or recombination sites and may additionally contain selectable marker genes.

While it may be optimal to express the Bs3 coding sequences using heterologous promoters, the native promoter sequences or truncations described herein below may be used. Such constructs can change expression levels of the Bs3 protein in the plant or plant cell. Thus, the phenotype of the plant or plant cell can be altered.

The termination region may be native with the transcriptional initiation region, may be native with the operably linked Bs3 polynucleotide of interest, may be native with the plant host, or may be derived from another source (i.e., foreign or heterologous) to the promoter, the Bs3 polynucleotide of interest, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core CaMV 35S promoter (Odell et al. (1985) *Nature* 313:

810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced Bs3 expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2): 141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize Tn2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10: 143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

Numerous plant transformation vectors and methods for transforming plants are available. See, for example, An, G. et al. (1986) *Plant Pysiol.*, 81:301-305; Fry, J., et al. (1987) *Plant Cell Rep.* 6:321-325; Block, M. (1988) *Theor. Appl Genet.* 76:767-774; Hinchee, et al. (1990) *Stadler. Genet. Symp.* 203212.203-212; Cousins, et al. (1991) *Aust. J. Plant Physiol.* 18:481-494; Chee, P. P. and Slightom, J. L. (1992) *Gene.* 118:255-260; Christou, et al. (1992) *Trends. Biotechnol.* 10:239-246; D'Halluin, et al. (1992) *Bio/Technol.* 10:309-314; Dhir, et al. (1992) *Plant Physiol.* 99:81-88; Casas et al. (1993) *Proc. Nat. Acad. Sci. USA* 90:11212-11216; Christou, P. (1993) *In Vitro Cell. Dev. Biol.-Plant;* 29P: 119-124; Davies, et al. (1993) *Plant Cell Rep.* 12:180-183; Dong, J. A. and Mchughen, A. (1993) *Plant Sci.* 91:139-148; Franklin, C. I. and Trieu, T. N. (1993) *Plant. Physiol.* 102:167; Golovkin, et al. (1993) *Plant Sci.* 90:41-52; *Guo Chin Sci. Bull.* 38:2072-2078; Asano, et al. (1994) *Plant Cell Rep.* 13; Ayeres N. M. and Park, W. D. (1994) *Crit. Rev. Plant. Sci.* 13:219-239; Barcelo, et al. (1994) *Plant. J.* 5:583-592; Becker, et al. (1994) *Plant. J.* 5:299-307; Borkowska et al. (1994) *Acta. Physiol Plant.* 16:225-230; Christou, P. (1994) *Agro. Food. Ind. Hi Tech.* 5: 17-27; Eapen et al. (1994) *Plant Cell Rep.* 13:582-586; Hartman, et al. (1994) *Bio-Technology* 12: 919923; Ritala, et al. (1994) *Plant. Mol. Biol.* 24:317-325; and Wan, Y. C. and Lemaux, P. G. (1994) *Plant Physiol.* 104:3748.

The methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods.

By "stable transformation" is intended that the polynucleotide construct introduced into a plant integrates into the genome of the plant and is capable of being inherited by progeny thereof. By "transient transformation" is intended that a polynucleotide construct introduced into a plant does not integrate into the genome of the plant.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed. In an embodiment of the invention, Bs3 polynucleotide is operably linked to a plant promoter that is known for high-level expression in a plant cell, and this construct is then introduced into a plant that is susceptible to an imidazolinone herbicide and a transformed plant is regenerated. The transformed plant is tolerant to exposure to a level of an imidazolinone herbicide that would kill or significantly injure an untransformed plant. This method can be applied to any plant species; however, it is most beneficial when applied to crop plants.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991) *Mol. Gen. Genet.,* 228: 104-112; Guerche et al., (1987) *Plant Science* 52: 111-116; Neuhause et al., (1987) *Theor. Appl Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701; *Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

Other suitable methods of introducing nucleotide sequences into plant cells and subsequent insertion into the plant genome include microinjection as Crossway et al. (1986) *Biotechniques* 4:320-334, electroporation as described by Riggs et al. (1986) *Proc. Natl. Acad. Sci. USA* 83:5602-5606, *Agrobacterium*-mediated transformation as described by Townsend et al., U.S. Pat. No. 5,563,055, Zhao et al., U.S. Pat. No. 5,981,840, direct gene transfer as described by Paszkowski et al. (1984) *EMBO J.* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); McCabe et al. (1988) *Biotechnology* 6:923-926); and Lec1 transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322, 783 and 5,324,646; Tomes et al. (1995) "Direct DNA Transfer into Intact Plant Cells via Microprojectile Bombardment," in *Plant Cell, Tissue, and Organ Culture: Fundamental Methods,* ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues,* ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a polynucleotide construct of the invention within a viral DNA or RNA molecule. It is recognized that the a Bs3 protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

In specific embodiments, the Bs3 sequences of the invention can be provided to a plant using a variety of transient transformation methods. Such transient transformation methods include, but are not limited to, the introduction of the Bs3 protein or variants and fragments thereof directly into the plant or the introduction of a Bs3 transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotide can be transiently transformed into the plant using techniques known in the art. Such techniques include viral vector system and *Agrobacterium tumefaciens*-mediated transient expression as described below.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide construct of the invention, for example, an expression cassette of the invention, stably incorporated into their genome.

The present invention may be used for transformation of any plant species, including, but not limited to, monocots and dicots. Examples of plant species of interest include, but are not limited to, peppers (*Capsicum* spp; e.g., *Capsicum annuum, C. baccatum, C. chinense, C. frutescens, C. pubescens*, and the like), tomatoes (*Lycopersicon esculentum*), tobacco (*Nicotiana tabacum*), eggplant (*Solanum melongena*), petunia (*Petunia* spp., e.g., *Petuniaxhybrida* or *Petunia hybrida*), corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutu*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruits, roots, root tips, anthers, and the like. Progeny, variants, and mutants of the regenerated plants are also included within the scope of the invention, provided that these parts comprise the introduced polynucleotides.

It is recognized that with these nucleotide sequences, antisense constructions, complementary to at least a portion of the messenger RNA (mRNA) for the Bs3 polynucleotide sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The invention is drawn to compositions and methods for inducing resistance to plant disease. By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Fungal pathogens, include but are not limited to, *Colletotrichum graminocola, Diplodia maydis, Fusarium graminearum,* and *Fusarium verticillioides*. Specific pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina,*

*Peronospora manshurica, Colletotrichum dematium (Colletotichum truncatum), Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassicicola, Pythium ultimum, Peronospora parasitica, Fusarium roseum, Alternaria alternata*; Alfalfa: *Clavibacter michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Verticillium albo-atrum, Xanthomonas campestris* p.v. *alfalfae, Aphanomyces euteiches, Stemphylium herbarum, Stemphylium alfalfae, Colletotrichum trifolii, Leptosphaerulina briosiana, Uromyces striatus, Sclerotinia trifoliorum, Stagonospora meliloti, Stemphylium botryosum, Leptotrichila medicaginis*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* fsp. *tritici, Puccinia graminis* fsp. *tritici, Puccinia recondita* fsp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmopora halstedii, Sclerotinia sclerotiorum, Aster Yellows, Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Colletotrichum graminicola, Fusarium moniliforme* var. *subglutinans, Erwinia stewartii, F. verticillioides, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis* O, T *(Cochliobolus heterostrophus), Helminthosporium carbonum* I, II & III *(Cochliobolus carbonum), Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, C. sublineolum, Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those. In addition, genes of interest include genes encoding enzymes and other proteins from plants and other sources including prokaryotes and other eukaryotes.

EXAMPLE 1

Isolation of the Wild-Type (Bs3) and Bs3-E Alleles of the Pepper Bs3 Gene

The Bs3 gene of pepper was isolated by from previously identified bacterial artificial chromosome (BAC) clones derived from the pepper (*Capsicum annuum*) cultivar Early Californian Wonder 30R (ECW-30R) that cover the Bs3 gene (Jordan et al. (2006) *Theor. Appl. Genet.* 113:895).

Materials and Methods
Plant Material and Infiltrations

Pepper (*Capsicum annuum*) plants of cultivar Early California Wonder (ECW) and the near-isogenic line ECW-30R containing the resistance gene Bs3 and *N. benthamiana* plants were grown in the greenhouse under standard conditions (day and night temperatures of 24 and 19° C., respectively), with 16 h of light and 60 to 40% humidity. Pepper cultivar ECW and the near-isogenic line ECW-30R seeds were provided by R. E. Stall (University of Florida, Gainesville). Six-week-old pepper plants were inoculated with *Xanthomonas* with $5 \times 10^8$ colony forming units/ml with a needle-less syringe. For cycloheximide treatment, leaf tissue was inoculated with a bacterial suspension as above, containing 50 µM cycloheximide.

Complementation with BAC Sub-Clones

BAC clone 128, which spans the Bs3 locus (Jordan et al. (2006) *Theor. Appl. Genet.* 113:895), was partially digested with HindIII (Fermentas, St. Leon-Rot, Germany). Restriction fragments of ≧10 kb were ligated into the binary-vector pVB61 (Schornack et al. (2004) *Plant J.* 37:46), which contains no promoter in its T-DNA region, and transformed into *A. tumefaciens* strain GV3101 (M. Holsters et al. (1980) *Plasmid* 3:212). Transformants ($OD_{600}$=0.8) were mixed 1:1 with an *A. tumefaciens* strain that delivers a T-DNA containing 35S-driven avrBs3. The mixture was injected into the lower side of fully expanded leaves of *C. annuum* cultivar ECW or *N. benthamiana* with a blunt syringe. *A. tumefaciens* strains that delivered the Bs3 gene induced an HR 3-4 days after inoculation.

Sequences and Alignments

Proteins with sequence similarity to pepper Bs3 were identified by BLAST searching of databases at the National Center for Biotechnology Information and the SOL Genomics Network FMO-like sequences from *Arabidopsis* were retrieved from TAIR. Sequences were aligned with the ClustalW program and the alignments visualized with the boxshade 3.21 program Tree-View 1.5.2 was used for generating a tree based on the ClustalW output.

Results and Discussion

For complementation-based-identification, fragments of a Bs3 containing BAC (Jordan et al. (2006) *Theor. Appl. Genet.* 113:895) were cloned into a plant transformation vector and were delivered into *Nicotiana benthamiana* leaves via *Agrobacterium tumefaciens*-mediated transient transformation. Two non-identical clones carrying the same coding sequence triggered an HR in *N. benthamiana* when co-transformed with avrBs3. A genomic DNA fragment containing only the predicted coding sequence and 1 kb of sequence upstream of the ATG mediated AvrBs3 recognition, confirming that this gene is Bs3 (FIG. 1A).

AvrBs3 mutants lacking the AD domain (AvrBs3ΔAD) or repeat units 11-14 (AvrBs3Δrep16) did not trigger HR in pepper Bs3 plants (Herbers et al. (1992) *Nature* 356:172; Szurek et al. (2001) *Plant J.* 26:523) and also failed to trigger HR in *N. benthamiana* when co-expressed with the cloned Bs3 gene (FIG. 1A). AvrBs4, which is 97% identical to AvrBs3 but is not recognized by pepper Bs3 genotypes (Bonas et al. (1993) *Mol. Gen. Genet.* 238:261), also did not trigger HR in *N. benthamiana* when co-expressed with Bs3 (FIG. 1A). Therefore, Bs3 mediates specific recognition of wild-type AvrBs3 both in pepper and *N. benthamiana* but not when AvrBs3 lacks the AD domain or repeat units 11-14; nor does it mediate recognition of the AvrBs3-like AvrBs4 protein. (FIG. 1C).

The Bs3 gene has three exons and two introns (FIG. 1D) is 342 amino acids long (FIG. 5) and is homologous to flavin-dependent monooxygenases (FMOs) (FIG. 6) (Schlaich (2007) *Trends Plant Sci.* in press). Bs3 is most closely related to FMOs of the *Arabidopsis* YUCCA family (FIG. 7) but lacks a stretch of 70 amino acids present in all related FMOs (FIG. 8).

Previous analysis showed that the AvrBs3-derivative AvrBs3 Δrep 16 (lacks repeat units 11-14) triggers HR in the pepper cultivar ECW but not in the near-isogenic Bs3-resistant cultivar ECW-30R (Herbers et al. (1992) *Nature* 356: 172). *N. benthamiana* was transformed with the ECW Bs3 allele (termed Bs3-E) including ~1 kb of the promoter and showed that it mediated recognition of AvrBs3Δrep16 but not AvrBs3 (FIG. 1B). Furthermore, AvrBs3Δrep16 lacking the C-terminal AD does not trigger HR when co-expressed with Bs3-E (FIG. 1B) and Bs3-E did not mediate recognition of AvrBs4. Thus, Bs3 and Bs3-E represent functional alleles with distinct recognition specificities (FIG. 1C). The coding sequences of the two Bs3 alleles differ by a single nucleotide conferring a non-synonymous change in exon 3, resulting in a leucine/phenylalanine difference (FIGS. 1D and 5). The promoter regions also differed by a 13-bp insertion in Bs3-E compared to Bs3, at position −50 relative to the transcription start site.

EXAMPLE 2

Construction and Analysis of Chimeric Bs3/Bs3-E and Bs3-E/Bs3 Genes

The Bs3 promoter was fused to the Bs3-E coding sequence and vice versa and co-transformed *N. benthamiana* with these chimeras in combination with avrBs3, avrBs3Δrep16 or the corresponding AD mutant derivatives.

Methods
Generation of Chimeric Constructs

Chimerical gene constructs were generated by splicing using overlap extension (SOE) PCR (Horton et al. (1989) *Gene* 77:61). Bs3 and Bs3-E promoters were amplified from genomic DNA of ECW and ECW-30R pepper cultivars, respectively, with the Phusion-polymerase and A1-fwd-PR (CTACGGAATAGCAGCATTAAGGCACATCAG; SEQ ID NO: 18) and B5-rev-PR (CATACGGAACACTGTATTGCT-TAAGG; SEQ ID NO: 19) primers. The coding regions were amplified with final-entry-01-fwd (ATGATGAATCAGAAT-TGCTTTAATTCTTGTTC; SEQ ID NO: 20) and final-entry-02-rev (CATTTGTTCTTTCCAAATTTTGGCAATATC; SEQ ID NO: 21) primers. PCR-products of the coding and promoter region were mixed in a 1:1 ratio and PCR amplified using A1-fwd-PR and final-entry-02-rev primers. The PCR-product was cloned into pENTR-D and, after sequencing, recombined into the T-DNA vector pGWB1.

Results and Discussion

The Bs3 promoter fused to the Bs3-E coding sequence mediated exclusively AvrBs3 recognition while the reciprocal chimera (Bs3-E promoter fused to the Bs3 coding sequence) mediated exclusively recognition of AvrBs3Δrep16 (FIG. 2). Thus, the promoter and not the coding region determines recognition specificity of the pepper Bs3 alleles.

EXAMPLE 3

Analysis of the Expression the Bs3 Gene in Pepper Leaves Inoculated with Virulent and Avirulent Xcv Strains Methods
RT-PCR Analysis of Xcv Infected Leaves The abaxial leaf surface of ECW and ECW-30R pepper plants was inoculated with Xcv strain 85-10 ($OD_{600}$=0.4) with a blunt syringe. Inoculations were carried out with isogenic Xcv strains expressing avrBs3 (pDS300F) (Van den Ackerveken et al. (1996) Cell 87:1307), avrBs3ΔAD (pDSF341) (Szurek et al. (2001) Plant J. 26:523), avrBs4 (pDSF200) (Schornack et al. (2004) Plant J. 37:46), avrBs3Δrep16 (pDSF316) (Herbers et al. (1992) Nature 356: 172) or avrBs3Δrep16ΔAD (pDSF317). Four leaf discs (5-mm diameter) were harvested 24 hours after inoculation and were used for each RNA-extraction using the Qiagen RNeasy Plant Miniprep kit (Qiagen, Hilden, Germany). RNA concentrations were determined with a ND-1000 spectrophotometer (Nanoprop Technologies, Rockland, Del., USA) and adjusted prior to cDNA synthesis. cDNA was synthesized by reverse transcription using an oligo dT-primer and the Revert Aid First Strand Synthesis Kit (Fermentas, St. Leon-Rot, Germany). For RT-PCR of Bs3 the Cand-7-01-fwd (ATGAATCAGAATTGCTTTAATTCTTGTTCA; SEQ ID NO: 22) and Cand-7-01-rev (TGATTCTTGTGCTACATTTGTTCTTTCC; SEQ ID NO: 23) primers were used. To amplify EF1α (used for RT-PCR normalization) primers RS-EFrt-F1 (AGTCAACTACCACTGGTCAC; SEQ ID NO: 24) and RS-EFrt-R1 (GTGCAGTAGTACTTAGTGGTC; SEQ ID NO: 25) were used. The 5' and 3' ends of the Bs3 and Bs3-E cDNAs were isolated by rapid amplification of cDNA ends (RACE) using the SMART RACE Kit (Clontech, Heidelberg, Germany).

Results and Discussion

Figure 3:
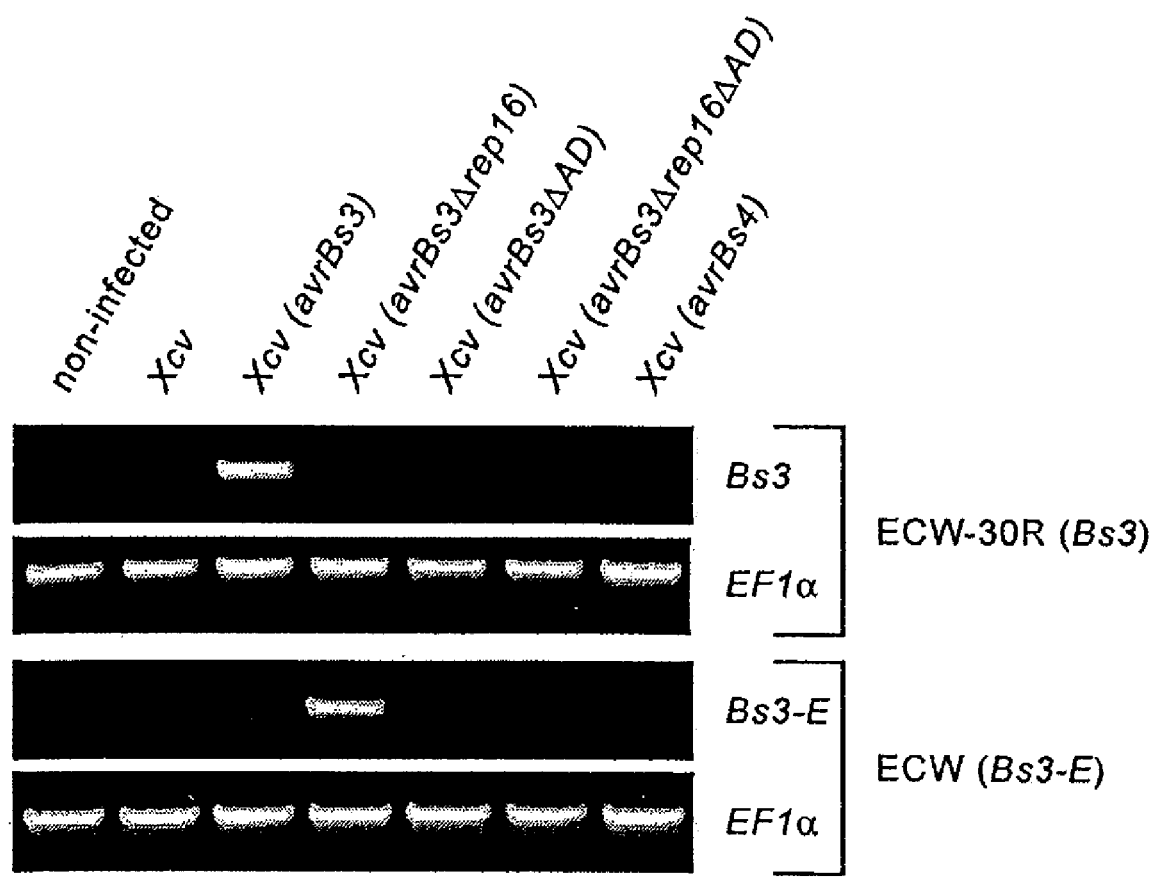

Semi-quantitative RT-PCR revealed strongly increased Bs3 transcript levels in pepper ECW-30R Bs3 plants upon infection with avrBs3-expressing, but not avrBs3Δrep16- or avrBs4-expressing Xcv strains (FIG. 3). Likewise, Bs3-E levels in ECW Bs3-E plants increased upon infection with avrBs3Δrep16-expressing Xcv strains but not when infected with avrBs3- or avrBs4-expressing Xcv strains. AD-mutant derivatives of avrBs3 and avrBs3Δrep16 did not induce accumulation of Bs3 or Bs3-E mRNA. Expression patterns were unaltered in the presence of the translation inhibitor cycloheximide (FIG. 9) indicating that accumulation of the Bs3 and Bs3-E transcripts was independent of de novo protein synthesis. Agrobacterium mediated transient co-expression of avrBs3 and a Bs3-GFP fusion under the control of the Bs3 promoter caused an increase in GFP fluorescence while delivery of Bs3-GFP on its own did not result in GFP fluorescence (FIG. 10). Together these data indicate that AvrBs3 and AvrBs3Δrep16 induce transcription of the respective R genes Bs3 and Bs3-E, and that the subsequent accumulation of these R proteins triggers HR. In agreement, constitutive expression of Bs3 or Bs3-E under the Cauliflower mosaic virus 35S promoter triggers an avr-independent HR (FIG. 11). Bs3 mutants were identified with single amino-acid replacements that were not compromised in protein stability but did no longer trigger HR when expressed in N. benthamiana (FIG. 12), indicating that the enzymatic activity of Bs3 is crucial to its function as a cell death inducer.

The pepper cultivar ECW-123R containing the R genes Bs1, Bs2 and Bs3 was infected with xanthomonads delivering either the structurally unrelated AvrBs1, AvrBs2 or AvrBs3 protein or none of these Avr proteins. RT-PCR showed that the Bs3-derived transcripts were detectable only upon infection with avrBs3-expressing Xcv strains (FIG. 14). Therefore Bs3 is not transcriptionally activated in the course of the Bs1- or Bs2-mediated HR.

EXAMPLE 4

Electrophoretic Mobility Shift Assays with AvrBs3 Proteins and Bs3 Promoter Fragments Methods
Electrophoretic Mobility Shift Assay (EMSA)

For DNA binding studies, GST fusion proteins were purified from E. coli BL21 with Glutathione Sepharose 4B (GE Healthcare Bio-Sciences AB, Uppsala) and the protein concentration was determined by Bradford protein assay (Bio-Rad, Hercules, Calif., U.S.A.). Complementary pairs of non-labeled or 5'-biotin-labeled oligonucleotides were annealed. EMSA was performed with the Light Shift® Chemiluminescent EMSA Kit (Pierce, Rockford) according to the manufacturer's protocol. The following parameters were used: Binding reactions contained 12 mM Tris-HCl (pH 7.5), 60 mM KCl, 1 mM DTT, 2.5% Glycerol, 5 mM $MgCl_2$, 50 ng/μl poly(dI·dC), 0.05% NP-40, 0.2 mM EDTA, 50 fmol biotin-labeled DNA, 0-10 pmol unlabeled DNA, 60-600 fmol GST fusion protein. The binding reactions were kept on ice for 10 min before biotin-labeled DNA was added. Gel electrophoresis was performed on a 6% native polyacrylamide gel. After blotting to a positively charged nylon membrane (Roche Diagnostics, Mannheim) the DNA was linked by baking at 100° C. for 1 h.

Results and Discussion

Figure 4:
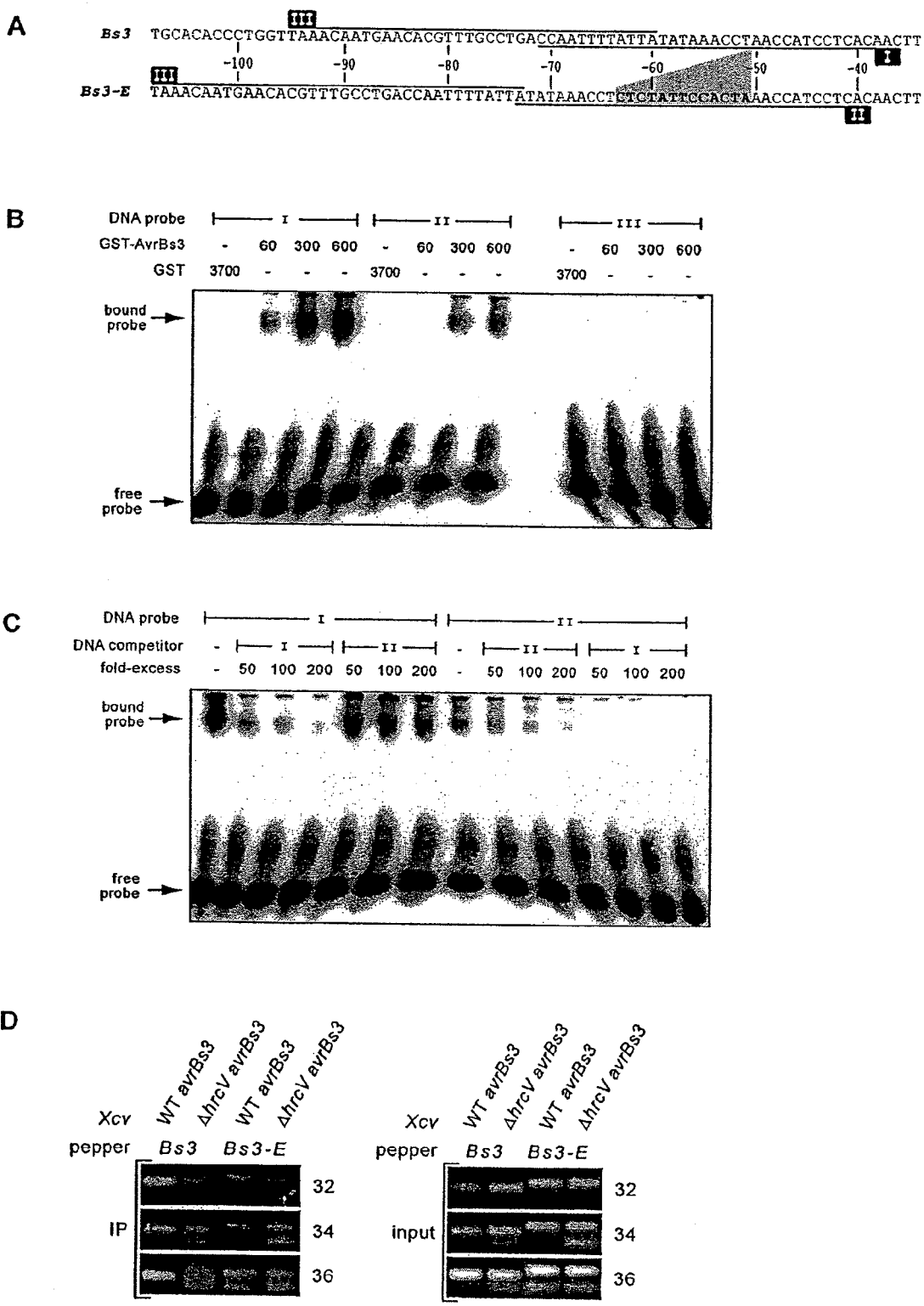

Electrophoretic mobility shift assays (EMSAs) with GST-AvrBs3 fusion protein and biotin-labeled Bs3 and Bs3-E promoter fragments (FIG. 4A) showed that AvrBs3 bound to both Bs3- and Bs3-E-derived promoter fragments containing the polymorphism, although affinity appeared higher for the Bs3-derived fragment (FIG. 4B). Competition assays with labeled Bs3-derived promoter fragments and non-labeled Bs3- and Bs3-E-derived promoter fragments and vice versa confirmed that AvrBs3 binds with high affinity to the Bs3-promoter fragment and with low affinity to the Bs3-E promoter fragment (FIG. 4C). In contrast, AvrBs3 did not bind to a DNA fragment from a non-polymorphic region of the Bs3 promoter (FIG. 4B). Furthermore EMSA studies showed that both AvrBs3 and AvrBs3Δrep16 have a higher affinity for the Bs3 compared to the Bs3-E promoter (FIGS. 4 and 13A-C). Therefore promoter binding per se of AvrBs3 or AvrBs3Δrep16 is not the basis for promoter activation specificity.

EXAMPLE 5

Chromatin Immunoprecipitation Assays

Methods
Chromatin Immunoprecipitation (ChIP)

For ChIP, 3 g pepper ECW or ECW-30R leaf material was harvested 12 hours post inoculation (hpi) with X. campestris pv. vesicatoria strains 82-8 and 82-8ΔhrcV, respectively. ChIP was performed as described (Offermann et al. (2006) Plant Physiol. 141:1078) with the following modifications: All buffers were supplemented with DTT instead of β-mercaptoethanol. 1× complete (Roche) was used as proteinase inhibitor. The chromatin was sonicated 6×20 sec with a Branson sonifier G250 (output control 3) and diluted 1:8.5 with ChIP dilution buffer. 100 μl pre-cleared chromatin solution was saved as input control, the rest was subjected to immunoprecipitation with 15 µl of affinity-purified and depleted AvrBs3-specific antibody Sta7 (Bonas et al. (1993) *Mol. Gen. Genet.* 238:261). The recovered DNA was analyzed by semi-quantitative PCR with input DNA as loading control. Different PCR cycle numbers were tested for both input and co-precipitated DNA.

Results and Discussion

Chromatin immunoprecipitation assays were performed by infiltrating pepper ECW-30R (Bs3) and ECW (Bs3-E) leaves either with avrBs3-expressing Xcv wild-type strains or with an isogenic hrcV mutant strain. HrcV is a conserved protein of the core T3S system with mutants incapable of delivering T3S effector proteins (Rossier et al. (1999) *Proc. Natl. Acad. Sci. USA* 96:9368). After immunoprecipitation with an AvrBs3 antibody (Knoop et al. (1991) *J. Bacteriol.* 173:7142), enrichment of the Bs3 but not the Bs3-E promoter region was detected by semi-quantitative PCR (FIG. 4D). This demonstrates that Xcv-delivered AvrBs3 binds to the Bs3 promoter in vivo with higher affinity than to the Bs3-E promoter. Given that Bs3 promoter enrichment was only detected in leaf material inoculated with wild-type, but not with the hrcV mutant strain, it was concluded that the Bs3-promoter is bound before cell lysis.

EXAMPLE 6

The Function and Structure of Bs3 Gene of Pepper

Isolation of the pepper Bs3 gene uncovered a mechanistically novel type of recognition mechanism and a structurally novel type of R protein that shares homology to FMOs. Recently, FMO1, an *Arabidopsis* protein that is sequence-related to Bs3 (see FIG. 6), was shown to be involved in pathogen defense (Bartsch et al. (2006) *Plant Cell* 18:1038; Koch et al. (2006) *Plant J.* 47:629; Mishina & Zeier (2006) *Plant Physiol.* 141: 1666). Thus FMO1 and Bs3 may have similar functions. However, FMO1 is transcriptionally induced by a variety of stimuli including virulent and avirulent microbial pathogens (Bartsch et al. (2006) *Plant Cell* 18:1038; Mishina & Zeier (2006) *Plant Physiol.* 141:1666; Olszak et al. (2006) *Plant Science* 170:614). In contrast, Bs3 is neither induced by virulent Xcv strains (FIG. 3) nor resistance reactions mediated by the pepper R genes Bs1 and Bs2 (see FIG. 14). Furthermore 35S-driven Bs3 alleles trigger an HR reaction (FIG. 11) while a 35S-driven FMO1 gene mediates broad-spectrum resistance but no HR (Bartsch et al. (2006) *Plant Cell* 18:1038; Koch et al. (2006) *Plant J.* 47:629). Thus, *Arabidopsis* FMO1 and pepper Bs3 differ with respect to their transcriptional regulation and function.

The results disclosed herein demonstrate that the bacterial effector protein AvrBs3 binds to and activates the promoter of the matching pepper R gene Bs3. Analysis of host genes that are unregulated by AvrBs3 ("upa" genes) in a compatible Xcv-pepper interaction (Marois et al. (2002) *Mol Plant-Microbe Interact.* 15:637-646; Kay et al. (2007) *Science* submitted) led to the identification of the upa-box (TATATAAACCN$_{2-3}$CC; SEQ ID NO: 17), a conserved DNA element that was shown to be bound by AvrBs3 and that is also present in the Bs3 promoter (FIG. 1D) (Kay et al. (2007) *Science* submitted). This suggests that binding of AvrBs3 to the upa-box is crucial for activation of corresponding promoters. However, binding of an AvrBs3-like protein does not necessarily result in promoter activation since AvrBs3Δrep16 binds with higher affinity to the Bs3 than to the Bs3-E promoter (FIG. 13) but only activates the Bs3-E and not the Bs3 promoter (FIG. 3). Because AvrBs3Δrep16 and AvrBs3 differ in their structure, it is postulated that upon DNA binding their functional domains (e.g., AD) are exposed at different promoter locations which may define whether or not AvrBs3Δrep16 and AvrBs3 are able to activate a given promoter. Additionally, given that the Bs3 promoter determines recognition specificity, the Bs3 promoter might be coevolving to maintain compatibility with rapidly changing AvrBs3-like proteins; similar to that seen in the NB-LRR proteins (McDowell & Simon (2006) *Mol Plant Pathol.* 7:437; Ellis et al. (2007) *Annu. Rev. Phytopathol.* 45:289).

It is likely that not only AvrBs3 but also other AvrBs3 homologs bind to and activate promoters of matching R genes. The recently isolated rice R gene Xa27, which mediates recognition of the AvrBs3-like AvrXa27 protein from *Xanthomonas oryzae* pv. *oryzae* (Gu et al. (2005) *Nature* 435:1122) is transcriptionally induced by AvrXa27 and thus it is tempting to speculate that the Xa27 promoter is a direct target of AvrXa27. However, whether AvrXa27 acts directly at the Xa27 promoter remains to be clarified.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

We claim:

1. An isolated nucleic acid molecule comprising a nucleotide sequence selected from the group consisting of:
   (a) the nucleotide sequence set forth in SEQ ID NO: 1, 3, 4, 9, 11, or 12;
   (b) a nucleotide sequence encoding the amino acid sequence set forth in SEQ ID NO: 2 or 10;
   (c) a nucleotide sequence comprising at least 90% nucleotide sequence identity to the nucleotide sequence set forth in SEQ ID NO: 1, 3, 4, 9, 11, and/or 12, wherein said nucleotide molecule encodes a polypeptide comprising flavin monooxygenase activity;
   (d) a nucleotide sequence encoding an amino acid sequence comprising at least 90% amino acid sequence identity to the amino acid sequence set forth in SEQ ID NO: 2 and/or 10, wherein said nucleotide molecule encodes a polypeptide comprising flavin monooxygenase activity; and
   (e) a nucleotide sequence that is fully complementary to the nucleotide sequence of any one of (a)-(d).

2. A transformed plant comprising a heterologous polynucleotide stably incorporated in its genome, said heterologous polynucleotide comprising a nucleotide molecule, said nucleotide molecule comprising a nucleotide sequence selected from the group consisting of:
   (a) the nucleotide sequence set forth in SEQ ID NO: 1, 3, 4, 9, 11, or 12;
   (b) a nucleotide sequence encoding the amino acid sequence set forth in SEQ ID NO: 2 or 10;
   (c) a nucleotide sequence comprising at least 90% nucleotide sequence identity to the nucleotide sequence set forth in SEQ ID NO: 1, 3, 4, 9, 11, and/or 12, wherein said nucleotide molecule encodes a polypeptide comprising flavin monooxygenase activity;
   (d) a nucleotide sequence encoding an amino acid sequence comprising at least 90% amino acid sequence identity to the amino acid sequence set forth in SEQ ID NO: 2 and/or 10, wherein said nucleotide molecule encodes a polypeptide comprising flavin monooxygenase activity;
   (e) a nucleotide sequence that is fully complementary to the nucleotide sequence of any one of (a)-(d).

3. The transformed plant of claim 2, wherein said heterologous polynucleotide further comprises a promoter operably linked to the nucleotide molecule.

4. The transformed plant of claim 3, wherein said promoter comprises a nucleotide sequence selected from the group consisting of:
   (i) the nucleotide sequence set forth in SEQ ID NO: 5, 6, 7, 13, 14, or 15;
   (ii) a nucleotide sequence comprising at least 90% nucleotide sequence identity to the nucleotide sequence set forth in SEQ ID NO: 5 and/or 13, wherein said nucleotide molecule comprises Bs3 promoter activity;
   (iii) a nucleotide sequence comprising a fragment of the nucleotide sequence set forth in SEQ ID NO: 5, wherein said fragment comprises a UPA box and said nucleotide molecule comprises Bs3 promoter activity; and
   (iv) a nucleotide sequence comprising a fragment of the nucleotide sequence set forth in SEQ ID NO: 13, wherein said fragment comprises a UPA box and said nucleotide molecule comprises Bs3 promoter activity.

5. The transformed plant of claim 2, wherein said plant is a monocot or a dicot.

6. The transformed plant of claim 2, wherein said transformed plant is selected from the group consisting of pepper, tomato, tobacco, broccoli, cauliflower, cabbage, cowpea, grape, canola, bean, soybean, rice, maize, wheat, barley, citrus, cotton, cassava, walnut, eggplant, petunia, and *Arabidopsis*.

7. A transformed seed comprising a heterologous polynucleotide stably incorporated in its genome, said heterologous polynucleotide comprising a nucleotide molecule, said nucleotide molecule comprising a nucleotide sequence selected from the group consisting of:
   (a) the nucleotide sequence set forth in SEQ ID NO: 1, 3, 4, 9, 11, or 12;
   (b) a nucleotide sequence encoding, the amino acid sequence set forth in SEQ ID NO: 2 or 10;
   (c) a nucleotide sequence comprising at least 90% nucleotide sequence identity to the nucleotide sequence set forth in SEQ ID NO: 1, 3, 4, 9, 11, and/or 12, wherein said nucleotide molecule encodes a polypeptide comprising flavin monooxygenase activity;
   (d) a nucleotide sequence encoding an amino acid sequence comprising at least 90% amino acid sequence identity to the amino acid sequence set forth in SEQ ID NO: 2 and/or t0, wherein said nucleotide molecule encodes a polypeptide comprising flavin monooxygenase activity;
   (e) a nucleotide sequence that is fully complementary to the nucleotide sequence of any one of (a)-(d).

8. A non-human host cell transformed with a polynucleotide construct comprising a nucleotide molecule, said nucleotide molecule comprising a nucleotide sequence selected from the group consisting of
   (a) the nucleotide sequence set forth in SEQ ID NO: 1, 3, 4, 9, 11, or 12;
   (b) a nucleotide sequence encoding the amino acid sequence set forth in SEQ ID NO: 2 or 10;
   (c) a nucleotide sequence comprising at least 90% nucleotide sequence identity to the nucleotide sequence set forth in SEQ ID NO: 1, 3, 4, 9, 11, and/or 12, wherein said nucleotide molecule encodes a polypeptide comprising flavin monooxygenase activity;
   (d) a nucleotide sequence encoding an amino acid sequence comprising at least 90% amino acid sequence identity to the amino acid sequence set forth in SEQ ID NO: 2 and/or 10, wherein said nucleotide molecule encodes a polypeptide comprising flavin monooxygenase activity;
   (e) a nucleotide sequence that is fully complementary to the nucleotide sequence of any one of (a)-(d).

9. The host cell of claim 8, wherein said polynucleotide construct further comprises a promoter operably linked to said nucleotide molecule, wherein said promoter drives expression of said nucleotide molecule in said host cell.

10. The host cell of claim 8, wherein said cell is a plant cell.

11. A method for increasing the resistance of a plant to at least one plant pathogen, said method comprising transforming a plant cell with a nucleotide molecule comprising a nucleotide sequence selected from the group consisting of:
(a) the nucleotide sequence set forth in SEQ ID NO: 1, 3, 9, or 11, said nucleotide sequence operably linked to a promoter that drives expression in a plant cell;
(b) a nucleotide sequence encoding the amino acid sequence set forth in SEQ ID NO: 2 or 10, said nucleotide sequence operably linked to a promoter that drives expression in a plant cell;
(c) a nucleotide sequence comprising at least 90% nucleotide sequence identity to the nucleotide sequence set forth in SEQ ID NO: 1, 3, 9, and/or 11, wherein said nucleotide sequence is operably linked to a promoter that drives expression in a plant cell and said nucleotide sequence encodes a polypeptide comprising flavin monooxygenase activity;
(d) a nucleotide sequence encoding an amino acid sequence comprising at least 90% amino acid sequence identity to the amino acid sequence set forth in SEQ ID NO: 2 and/or 10, wherein said nucleotide sequence is operably linked to a promoter that drives expression in a plant cell and said nucleotide sequence encodes a polypeptide comprising flavin monooxygenase activity;
(e) the nucleotide sequence set forth in SEQ ID NO: 4 or 12; and
(f) a nucleotide sequence comprising at least 90% nucleotide sequence identity to the nucleotide sequence set forth in SEQ ID NO: 4 and/or 12, wherein said nucleotide sequence encodes a polypeptide comprising flavin monooxygenase activity.

12. The method of claim 11, further comprising regenerating a transformed plant from said transformed cell.

13. The method of claim 11, wherein the nucleotide molecule further comprises an operably linked promoter.

14. The method of claim 13, wherein said promoter is a pathogen-inducible promoter.

15. The method of claim 13, wherein said promoter comprises a nucleotide sequence selecting from the group consisting of SEQ ID NOS: 5-7 and 13-15.

16. The method of claim 11, wherein said plant pathogen is *Xanthomonas campestris*.

17. The method of claim 11, wherein said transformed plant further comprises a nucleotide sequence encoding the Bs2 protein.

18. A method for expressing a gene of interest in a plant or plant cell, said method comprising transforming a plant cell with a polynucleotide construct comprising a promoter operably linked to a gene of interest, wherein said promoter comprises a nucleotide sequence selected from the group consisting of:
(a) the nucleotide sequence set forth in SEQ ID NO: 5, 6, 7, 13, 14, or 15;
(b) a nucleotide sequence comprising at least 90% nucleotide sequence identity to the nucleotide sequence set forth in SEQ ID NO: 5 and/or 13, wherein said nucleotide molecule comprises Bs3 promoter activity;
(c) a nucleotide sequence comprising a fragment of the nucleotide sequence set forth in SEQ ID NO: 5, wherein said fragment comprises a UPA box and said nucleotide molecule comprises Bs3 promoter activity; and
(d) a nucleotide sequence comprising a fragment of the nucleotide sequence set forth in SEQ ID NO: 13, wherein said fragment comprises a UPA box and said nucleotide molecule comprises Bs3 promoter activity.

19. The method of claim 18, further comprising regenerating said transformed cell into a transformed plant.

20. The method of claim 18, wherein said gene of interest encodes the Bs3 protein.

21. A method for high-level gene expression in a plant or plant cell, said method comprising transforming a plant cell with a first polynucleotide construct and a second polynucleotide construct, wherein said first polynucleotide construct comprises a first promoter operably linked to a nucleotide sequence encoding AvrBs3 and said second polynucleotide construct comprises a second promoter operably linked to a gene of interest, wherein said gene of interest is expressed in said plant or plant cell, wherein said second promoter comprises a nucleotide sequence selected from the group consisting of:
(a) the nucleotide sequence set forth in SEQ ID NO: 5, 6, 7, 13, 14, or 15;
(b) a nucleotide sequence comprising at least 90% nucleotide sequence identity to the nucleotide sequence set forth in SEQ ID NO: 5 and/or 13, wherein said nucleotide molecule comprises Bs3 promoter activity;
(c) a nucleotide sequence comprising a fragment of the nucleotide sequence set forth in SEQ ID NO: 5, wherein said fragment comprises a UPA box and said nucleotide molecule comprises Bs3 promoter activity; and
(d) a nucleotide sequence comprising a fragment of the nucleotide sequence set forth in SEQ ID NO: 13, wherein said fragment comprises a UPA box and said nucleotide molecule comprises Bs3 promoter activity.

22. The method of claim 21, wherein said gene of interest is expressed at a high-level when compared to a plant lacking said first polynucleotide construct.

23. The method of claim 21, further comprising regenerating said transformed cell into a transformed plant.

24. The method of claim 21, wherein said first promoter is selected from the group consisting of constitutive promoters, wound-inducible promoters, pathogen-inducible promoters, chemical-regulated promoters, chemical-inducible promoters, and tissue-preferred promoters.

25. The method of claim 21, wherein said first promoter comprises a nucleotide sequence selected from the group consisting of:
(a) the nucleotide sequence set forth in SEQ ID NO: 5, 6, 7, 13, 14, or 15;
(b) a nucleotide sequence comprising at least 90% nucleotide sequence identity to the nucleotide sequence set forth in SEQ ID NO: 5, and/or 13, wherein said nucleotide molecule comprises Bs3 promoter activity;
(c) a nucleotide sequence comprising a fragment of the nucleotide sequence set forth in SEQ ID NO: 5, wherein said fragment comprises a UPA box and said nucleotide molecule comprises Bs3 promoter activity; and
(d) a nucleotide sequence comprising a fragment of the nucleotide sequence set forth in SEQ ID NO: 13, wherein said fragment comprises a UPA box and said nucleotide molecule comprises Bs3 promoter activity.

26. A method for causing cell death in a plant part of interest comprising transforming a plant cell with polynucleotide construct comprising a nucleotide molecule operably linked to a promoter that drives gene expression in a plant cell, wherein cell death occurs in the plant part of interest upon expression of said nucleotide sequence in said plant part of interest, and wherein said nucleotide molecule is selected from the group consisting of:
(a) the nucleotide sequence set forth in SEQ ID NO: 1, 3, 4, 9, 11, or 12;
(b) a nucleotide sequence encoding the amino acid sequence set forth in SEQ ID NO: 2 or 10;

(c) a nucleotide sequence comprising at least 90% nucleotide sequence identity to the nucleotide sequence set forth in SEQ ID NO: 1, 3, 4, 9, 11, and/or 12, wherein said nucleotide molecule encodes a polypeptide comprising flavin monooxygenase activity; and (d) a nucleotide sequence encoding an amino acid sequence comprising at least 90% amino acid sequence identity to the amino acid sequence set forth in SEQ ID NO: 2 and/or 10, wherein said nucleotide molecule encodes a polypeptide comprising flavin monooxygenase activity.

27. The method of claim 26, further comprising regenerating a transformed plant from said transformed cell.

28. The method of claim 26, wherein said promoter is selected from the group consisting of tissue preferred promoters, chemical-inducible promoters, and pathogen-inducible promoters.

29. An isolated nucleic acid molecule comprising a nucleotide sequence selected from the group consisting of
(a) the nucleotide sequence set forth in SEQ ID NO: 5, 6, 7, 13, 14, or 15;
(b) a nucleotide sequence comprising at least 90% nucleotide sequence identity to the nucleotide sequence set forth in SEQ ID NO: 5 and/or 13, wherein said nucleotide molecule comprises Bs3 promoter activity;
(c) a nucleotide sequence comprising a fragment of the nucleotide sequence set forth in SEQ ID NO: 5, wherein said fragment comprises a UPA box and said nucleotide molecule comprises Bs3 promoter activity; and
(d) a nucleotide sequence comprising a fragment of the nucleotide sequence set forth in SEQ ID NO: 13, wherein said fragment comprises a UPA box and said nucleotide molecule comprises Bs3 promoter activity;
(e) a nucleotide sequence that is fully complementary to the nucleotide sequence of any one of (a)-(d).

30. A transformed plant comprising a heterologous polynucleotide stably incorporated in its genome, said heterologous polynucleotide comprising a nucleotide molecule, said nucleotide molecule comprising a nucleotide sequence selected from the group consisting of:
(a) the nucleotide sequence set forth in SEQ ID NO: 5, 6, 7, 13, 14, or 15;
(b) a nucleotide sequence comprising at least 90% nucleotide sequence identity to the nucleotide sequence set forth in SEQ ID NO: 5 and/or 13, wherein said nucleotide molecule comprises Bs3 promoter activity;
(c) a nucleotide sequence comprising a fragment of the nucleotide sequence set forth in SEQ ID NO: 5, wherein said fragment comprises a UPA box and said nucleotide molecule comprises Bs3 promoter activity; and
(d) a nucleotide sequence comprising a fragment of the nucleotide sequence set forth in SEQ ID NO: 13, wherein said fragment comprises a UPA box and said nucleotide molecule comprises Bs3 promoter activity;
(e) a nucleotide sequence that is fully complementary to the nucleotide sequence of any one of (a)-(d).

31. The transformed plant of claim 30, wherein said heterologous polynucleotide further comprises a gene of interest operably linked to the nucleotide molecule.

32. The transformed plant of claim 31, wherein said gene of interest comprises a nucleotide sequence selected from the group consisting of:
(a) the nucleotide sequence set forth in SEQ ID NO: 1, 3, 9, or 11;
(b) a nucleotide sequence encoding the amino acid sequence set forth in SEQ ID NO: 2 or 10;

(c) a nucleotide sequence comprising at least 90% nucleotide sequence identity to the nucleotide sequence set forth in SEQ ID NO: 1, 3, 9, and/or 11, wherein said nucleotide sequence encodes a polypeptide comprising flavin monooxygenase activity; and
(d) a nucleotide sequence encoding an amino acid sequence comprising at least 90% amino acid sequence identity to the amino acid sequence set forth in SEQ ID NO: 2 and/or 10, wherein said nucleotide sequence encodes a polypeptide comprising flavin monooxygenase activity.

33. The transformed plant of claim 30, wherein said plant is a monocot or a dicot.

34. The transformed plant of claim 30, wherein said transformed plant is selected from the group consisting of pepper, tomato, tobacco, broccoli, cauliflower, cabbage, cowpea, grape, canola, bean, soybean, rice, maize, wheat, barley, citrus, cotton, cassava, walnut, eggplant, petunia, and *Arabidopsis*.

35. A transformed seed comprising a heterologous polynucleotide stably incorporated in its genome, said heterologous polynucleotide comprising a nucleotide molecule, said nucleotide molecule comprising a nucleotide sequence selected from the group consisting of:
(a) the nucleotide sequence set forth in SEQ ID NO: 5, 6, 7, 13, 14 or 15;
(b) a nucleotide sequence having at least 90% nucleotide sequence identity to the nucleotide sequence set forth in SEQ ID NO: 5 and/or 13, wherein said nucleotide molecule comprises Bs3 promoter activity;
(c) a nucleotide sequence comprising a fragment of the nucleotide sequence set forth in SEQ ID NO: 5, wherein said fragment comprises a UPA box and said nucleotide molecule comprises Bs3 promoter activity;
(d) a nucleotide sequence comprising a fragment of the nucleotide sequence set forth in SEQ ID NO: 13, wherein said fragment comprises a UPA box and said nucleotide molecule comprises Bs3 promoter activity;
(e) a nucleotide sequence that is fully complementary to the nucleotide sequence of any one of (a)-(d).

36. A non-human host cell transformed with a polynucleotide construct comprising a nucleotide molecule, said nucleotide molecule comprising a nucleotide sequence selected from the group consisting of:
(a) the nucleotide sequence set forth in SEQ ID NO: 5, 6, 7, 13, 14, or 15;
(b) a nucleotide sequence comprising at least 90% nucleotide sequence identity to the nucleotide sequence set forth in SEQ ID NO: 5 and/or 13, wherein said nucleotide molecule comprises Bs3 promoter activity;
(c) a nucleotide sequence comprising a fragment of the nucleotide sequence set forth in SEQ ID NO: 5, wherein said fragment comprises a UPA box and said nucleotide molecule comprises Bs3 promoter activity; and
(d) a nucleotide sequence comprising a fragment of the nucleotide sequence set forth in SEQ ID NO: 13, wherein said fragment comprises a UPA box and said nucleotide molecule comprises Bs3 promoter activity;
(e) a nucleotide sequence that is fully complementary to the nucleotide sequence of an one of (a)-(d).

37. The host cell of claim 36, wherein said polynucleotide construct further comprises a gene of interest operably linked to said nucleotide molecule.

38. The host cell of claim 36, wherein said cell is a plant cell.

* * * * *

UNITED STATES PATENT AND TRADEMARK OFFICE
CERTIFICATE OF CORRECTION

PATENT NO.         : 8,198,510 B2
APPLICATION NO.    : 12/238682
DATED              : June 12, 2012
INVENTOR(S)        : Lahaye et al.

It is certified that error appears in the above-identified patent and that said Letters Patent is hereby corrected as shown below:

Column 2, line 20, "(Bs)" should read --(Bs1--;

Column 27, line 66, "hirsutu" should read --hirsutum--; and

Column 27, line 66, "cassaya" should read --cassava--.

Signed and Sealed this
Fourteenth Day of August, 2012

David J. Kappos
*Director of the United States Patent and Trademark Office*